(12) United States Patent
Shaheen et al.

(10) Patent No.: US 10,550,155 B2
(45) Date of Patent: Feb. 4, 2020

(54) ANTICANCER PEPTIDES

(71) Applicants: Farzana Shaheen, Karachi (PK); Muhammad Nadeem-ul-Haque, Karachi (PK); Shabana U. Simjee, Karachi (PK); Aqeel Ahmed, Karachi (PK); Zafar Ali Shah, Karachi (PK); Almas Jabeen, Karachi (PK); Muhammad Iqbal Choudhary, Karachi (PK)

(72) Inventors: Farzana Shaheen, Karachi (PK); Muhammad Nadeem-ul-Haque, Karachi (PK); Shabana U. Simjee, Karachi (PK); Aqeel Ahmed, Karachi (PK); Zafar Ali Shah, Karachi (PK); Almas Jabeen, Karachi (PK); Muhammad Iqbal Choudhary, Karachi (PK)

( * ) Notice: Subject to any disclaimer, the term of this patent is extended or adjusted under 35 U.S.C. 154(b) by 0 days.

(21) Appl. No.: 15/937,281

(22) Filed: Mar. 27, 2018

(65) Prior Publication Data

US 2019/0300572 A1    Oct. 3, 2019

(51) Int. Cl.
| | | |
|---|---|---|
| *C07K 7/08* | (2006.01) | |
| *C07K 14/00* | (2006.01) | |
| *C07K 19/00* | (2006.01) | |
| *A61K 38/10* | (2006.01) | |
| *A61K 38/16* | (2006.01) | |
| *A61P 35/00* | (2006.01) | |
| *A61K 38/00* | (2006.01) | |

(52) U.S. Cl.
CPC ............ *C07K 7/08* (2013.01); *A61P 35/00* (2018.01); *A61K 38/00* (2013.01)

(58) Field of Classification Search
CPC ......... A61K 38/10; A61K 38/16; C07K 7/08; C07K 14/00; C07K 19/00; C07K 2319/00
USPC ......... 514/21.3, 21.4, 21.5, 19.2, 19.3, 19.4, 514/19.5, 19.6, 19.8; 530/324, 326, 327, 530/387.3
See application file for complete search history.

(56) References Cited

U.S. PATENT DOCUMENTS 9,522,942 B2 *   12/2016   Ladram ............... C07K 14/463

* cited by examiner

*Primary Examiner* — Julie Ha
(74) *Attorney, Agent, or Firm* — Sarfaraz K. Niazi

(57) ABSTRACT

This invention provides new anticancer analogs of antimicrobial peptide temporin-SHa. New analogs (SEQ ID NOs: 2-6) of temporin SHa and, two different conjugates (7 & 8) comprising of monomeric and dimeric form of SEQ ID NO 4 with cancer targeting ligand were identified as anticancer peptides.

3 Claims, 10 Drawing Sheets

Specification includes a Sequence Listing.

SEQ ID NO: 1  $R^4 = R^7 = R^{10} =$ Gly
SEQ ID NO: 2  $R^4 =$ D-ala, $R^7 = R^{10} =$ Gly
SEQ ID NO: 3  $R^7 =$ D-ala, $R^4 = R^{10} =$ Gly
SEQ ID NO: 4  $R^{10} =$ D-ala, $R^4 = R^7 =$ Gly
SEQ ID NO: 5  $R^4 = R^7 =$ D-ala, $R^{10} =$ Gly
SEQ ID NO: 6  $R^4 = R^7 = R^{10} =$ D-ala Conjugate 7

Conjugate 8

SEQUENCE LISTING

<160> NUMBER OF SEQ ID NOS: 76

<210> SEQ ID NO 1
<211> LENGTH: 13
<212> TYPE: PRT
<213> ORGANISM: artificial sequence
<220> FEATURE:
<223> OTHER INFORMATION: synthetic

<400> SEQUENCE: 1

Phe Leu Ser Gly Ile Val Gly Met Leu Gly Lys Leu Phe
1               5                   10

<210> SEQ ID NO 2
<211> LENGTH: 13
<212> TYPE: PRT
<213> ORGANISM: artificial sequence
<220> FEATURE:
<223> OTHER INFORMATION: synthetic

<400> SEQUENCE: 2

Phe Leu Ser Ala Ile Val Gly Met Leu Gly Lys Leu Phe
1               5                   10

<210> SEQ ID NO 3
<211> LENGTH: 13
<212> TYPE: PRT

```
<213> ORGANISM: artificial sequence
<220> FEATURE:
<223> OTHER INFORMATION: synthetic

<400> SEQUENCE: 3

Phe Leu Ser Gly Ile Val Ala Met Leu Gly Lys Leu Phe
1               5                   10

<210> SEQ ID NO 4
<211> LENGTH: 13
<212> TYPE: PRT
<213> ORGANISM: artificial sequence
<220> FEATURE:
<223> OTHER INFORMATION: synthetic

<400> SEQUENCE: 4

Phe Leu Ser Gly Ile Val Gly Met Leu Ala Lys Leu Phe
1               5                   10

<210> SEQ ID NO 5
<211> LENGTH: 13
<212> TYPE: PRT
<213> ORGANISM: artificial sequence
<220> FEATURE:
<223> OTHER INFORMATION: synthetic

<400> SEQUENCE: 5

Phe Leu Ser Ala Ile Val Ala Met Leu Gly Lys Leu Phe
1               5                   10

<210> SEQ ID NO 6
<211> LENGTH: 13
<212> TYPE: PRT
<213> ORGANISM: artificial sequence
<220> FEATURE:
<223> OTHER INFORMATION: synthetic

<400> SEQUENCE: 6

Phe Leu Ser Ala Ile Val Ala Met Leu Ala Lys Leu Phe
1               5                   10

<210> SEQ ID NO 7
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: Linked to Seq-ID No. 4 at Lysine (residue 9)

<400> SEQUENCE: 7

Trp Leu Glu Ala Ala Tyr Gln Lys Phe Leu
1               5                   10

<210> SEQ ID NO 8
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: Linked to Seq_ID 4 dimer at Lysine (residue 9)

<400> SEQUENCE: 8
```

-continued

Trp Leu Glu Ala Ala Tyr Gln Lys Phe Leu
1               5                   10

<210> SEQ ID NO 9
<211> LENGTH: 10
<212> TYPE: PRT
<213> ORGANISM: artificial sequence
<220> FEATURE:
<223> OTHER INFORMATION: synthetic

<400> SEQUENCE: 9

Trp Leu Glu Ala Ala Tyr Gln Lys Phe Leu
1               5                   10

<210> SEQ ID NO 10
<211> LENGTH: 10
<212> TYPE: PRT
<213> ORGANISM: artificial sequence
<220> FEATURE:
<223> OTHER INFORMATION: synthetic

<400> SEQUENCE: 10

Ala Ile Val Gly Met Leu Gly Lys Leu Phe
1               5                   10

<210> SEQ ID NO 11
<211> LENGTH: 9
<212> TYPE: PRT
<213> ORGANISM: artificial sequence
<220> FEATURE:
<223> OTHER INFORMATION: synthetic

<400> SEQUENCE: 11

Ile Val Gly Met Leu Gly Lys Leu Phe
1               5

<210> SEQ ID NO 12
<211> LENGTH: 8
<212> TYPE: PRT
<213> ORGANISM: artificial sequence
<220> FEATURE:
<223> OTHER INFORMATION: synthetic

<400> SEQUENCE: 12

Val Gly Met Leu Gly Lys Leu Phe
1               5

<210> SEQ ID NO 13
<211> LENGTH: 6
<212> TYPE: PRT
<213> ORGANISM: artificial sequence
<220> FEATURE:
<223> OTHER INFORMATION: synthetic

<400> SEQUENCE: 13

Phe Leu Ser Ala Ile Val
1               5

<210> SEQ ID NO 14
<211> LENGTH: 6
<212> TYPE: PRT
<213> ORGANISM: artificial sequence
<220> FEATURE:
<223> OTHER INFORMATION: synthetic

<400> SEQUENCE: 14

Met Leu Gly Lys Leu Phe

```
1               5
```

```
<210> SEQ ID NO 15
<211> LENGTH: 8
<212> TYPE: PRT
<213> ORGANISM: artificial sequence
<220> FEATURE:
<223> OTHER INFORMATION: synthetic

<400> SEQUENCE: 15

Phe Leu Ser Ala Ile Val Gly Met
1               5

<210> SEQ ID NO 16
<211> LENGTH: 5
<212> TYPE: PRT
<213> ORGANISM: artificial sequence
<220> FEATURE:
<223> OTHER INFORMATION: synthetic

<400> SEQUENCE: 16

Leu Gly Lys Leu Phe
1               5

<210> SEQ ID NO 17
<211> LENGTH: 9
<212> TYPE: PRT
<213> ORGANISM: artificial sequence
<220> FEATURE:
<223> OTHER INFORMATION: synthetic

<400> SEQUENCE: 17

Phe Leu Ser Ala Ile Val Gly Met Leu
1               5

<210> SEQ ID NO 18
<211> LENGTH: 4
<212> TYPE: PRT
<213> ORGANISM: artificial sequence
<220> FEATURE:
<223> OTHER INFORMATION: synthetic

<400> SEQUENCE: 18

Gly Lys Leu Phe
1

<210> SEQ ID NO 19
<211> LENGTH: 10
<212> TYPE: PRT
<213> ORGANISM: artificial sequence
<220> FEATURE:
<223> OTHER INFORMATION: synthetic

<400> SEQUENCE: 19

Phe Leu Ser Ala Ile Val Gly Met Leu Gly
1               5                   10

<210> SEQ ID NO 20
<211> LENGTH: 11
<212> TYPE: PRT
<213> ORGANISM: artificial sequence
<220> FEATURE:
<223> OTHER INFORMATION: synthetic

<400> SEQUENCE: 20

Phe Leu Ser Ala Ile Val Gly Met Leu Gly Lys
1               5                   10
```

<210> SEQ ID NO 21
<211> LENGTH: 12
<212> TYPE: PRT
<213> ORGANISM: artificial sequence
<220> FEATURE:
<223> OTHER INFORMATION: synthetic

<400> SEQUENCE: 21

Phe Leu Ser Ala Ile Val Gly Met Leu Gly Lys Leu
1               5                   10

<210> SEQ ID NO 22
<211> LENGTH: 13
<212> TYPE: PRT
<213> ORGANISM: artificial sequence
<220> FEATURE:
<223> OTHER INFORMATION: synthetic

<400> SEQUENCE: 22

Phe Leu Ser Ala Ile Val Gly Met Leu Gly Lys Leu Phe
1               5                   10

<210> SEQ ID NO 23
<211> LENGTH: 12
<212> TYPE: PRT
<213> ORGANISM: artificial sequence
<220> FEATURE:
<223> OTHER INFORMATION: synthetic

<400> SEQUENCE: 23

Leu Ser Gly Ile Val Ala Met Leu Gly Lys Leu Phe
1               5                   10

<210> SEQ ID NO 24
<211> LENGTH: 10
<212> TYPE: PRT
<213> ORGANISM: artificial sequence
<220> FEATURE:
<223> OTHER INFORMATION: synthetic

<400> SEQUENCE: 24

Gly Ile Val Ala Met Leu Gly Lys Leu Phe
1               5                   10

<210> SEQ ID NO 25
<211> LENGTH: 9
<212> TYPE: PRT
<213> ORGANISM: artificial sequence
<220> FEATURE:
<223> OTHER INFORMATION: synthetic

<400> SEQUENCE: 25

Ile Val Ala Met Leu Gly Lys Leu Phe
1               5

<210> SEQ ID NO 26
<211> LENGTH: 4
<212> TYPE: PRT
<213> ORGANISM: artificial sequence
<220> FEATURE:
<223> OTHER INFORMATION: synthetic

<400> SEQUENCE: 26

Phe Leu Ser Gly
1

<210> SEQ ID NO 27
<211> LENGTH: 8
<212> TYPE: PRT
<213> ORGANISM: artificial sequence
<220> FEATURE:
<223> OTHER INFORMATION: synthetic

<400> SEQUENCE: 27

Val Ala Met Leu Gly Lys Leu Phe
1               5

<210> SEQ ID NO 28
<211> LENGTH: 5
<212> TYPE: PRT
<213> ORGANISM: artificial sequence
<220> FEATURE:
<223> OTHER INFORMATION: synthetic

<400> SEQUENCE: 28

Phe Leu Ser Gly Ile
1               5

<210> SEQ ID NO 29
<211> LENGTH: 7
<212> TYPE: PRT
<213> ORGANISM: artificial sequence
<220> FEATURE:
<223> OTHER INFORMATION: synthetic

<400> SEQUENCE: 29

Ala Met Leu Gly Lys Leu Phe
1               5

<210> SEQ ID NO 30
<211> LENGTH: 7
<212> TYPE: PRT
<213> ORGANISM: artificial sequence
<220> FEATURE:
<223> OTHER INFORMATION: synthetic

<400> SEQUENCE: 30

Phe Leu Ser Gly Ile Val Ala
1               5

<210> SEQ ID NO 31
<211> LENGTH: 6
<212> TYPE: PRT
<213> ORGANISM: artificial sequence
<220> FEATURE:
<223> OTHER INFORMATION: synthetic

<400> SEQUENCE: 31

Met Leu Gly Lys Leu Phe
1               5

<210> SEQ ID NO 32
<211> LENGTH: 7
<212> TYPE: PRT
<213> ORGANISM: artificial sequence
<220> FEATURE:
<223> OTHER INFORMATION: synthetic

<400> SEQUENCE: 32

Phe Leu Ser Gly Ile Val Ala
1               5

```
<210> SEQ ID NO 33
<211> LENGTH: 5
<212> TYPE: PRT
<213> ORGANISM: artificial sequence
<220> FEATURE:
<223> OTHER INFORMATION: synthetic

<400> SEQUENCE: 33

Leu Gly Lys Leu Phe
1               5

<210> SEQ ID NO 34
<211> LENGTH: 9
<212> TYPE: PRT
<213> ORGANISM: artificial sequence
<220> FEATURE:
<223> OTHER INFORMATION: synthetic

<400> SEQUENCE: 34

Phe Leu Ser Gly Ile Val Ala Met Leu
1               5

<210> SEQ ID NO 35
<211> LENGTH: 10
<212> TYPE: PRT
<213> ORGANISM: artificial sequence
<220> FEATURE:
<223> OTHER INFORMATION: synthetic

<400> SEQUENCE: 35

Phe Leu Ser Gly Ile Val Ala Met Leu Gly
1               5                   10

<210> SEQ ID NO 36
<211> LENGTH: 11
<212> TYPE: PRT
<213> ORGANISM: artificial sequence
<220> FEATURE:
<223> OTHER INFORMATION: synthetic

<400> SEQUENCE: 36

Phe Leu Ser Gly Ile Val Ala Met Leu Gly Lys
1               5                   10

<210> SEQ ID NO 37
<211> LENGTH: 11
<212> TYPE: PRT
<213> ORGANISM: artificial sequence
<220> FEATURE:
<223> OTHER INFORMATION: synthetic

<400> SEQUENCE: 37

Phe Leu Ser Gly Ile Val Ala Met Leu Gly Lys
1               5                   10

<210> SEQ ID NO 38
<211> LENGTH: 13
<212> TYPE: PRT
<213> ORGANISM: artificial sequence
<220> FEATURE:
<223> OTHER INFORMATION: synthetic

<400> SEQUENCE: 38

Phe Leu Ser Gly Ile Val Ala Met Leu Gly Lys Leu Phe
1               5                   10

<210> SEQ ID NO 39
```

```
<211> LENGTH: 11
<212> TYPE: PRT
<213> ORGANISM: artificial sequence
<220> FEATURE:
<223> OTHER INFORMATION: synthetic

<400> SEQUENCE: 39

Ser Gly Ile Val Gly Met Leu Ala Lys Leu Phe
1               5                   10

<210> SEQ ID NO 40
<211> LENGTH: 10
<212> TYPE: PRT
<213> ORGANISM: artificial sequence
<220> FEATURE:
<223> OTHER INFORMATION: synthetic

<400> SEQUENCE: 40

Gly Ile Val Gly Met Leu Ala Lys Leu Phe
1               5                   10

<210> SEQ ID NO 41
<211> LENGTH: 7
<212> TYPE: PRT
<213> ORGANISM: artificial sequence
<220> FEATURE:
<223> OTHER INFORMATION: synthetic

<400> SEQUENCE: 41

Gly Met Leu Ala Lys Leu Phe
1               5

<210> SEQ ID NO 42
<211> LENGTH: 6
<212> TYPE: PRT
<213> ORGANISM: artificial sequence
<220> FEATURE:
<223> OTHER INFORMATION: synthetic

<400> SEQUENCE: 42

Met Leu Ala Lys Leu Phe
1               5

<210> SEQ ID NO 43
<211> LENGTH: 5
<212> TYPE: PRT
<213> ORGANISM: artificial sequence
<220> FEATURE:
<223> OTHER INFORMATION: synthetic

<400> SEQUENCE: 43

Leu Ala Lys Leu Phe
1               5

<210> SEQ ID NO 44
<211> LENGTH: 9
<212> TYPE: PRT
<213> ORGANISM: artificial sequence
<220> FEATURE:
<223> OTHER INFORMATION: synthetic

<400> SEQUENCE: 44

Phe Leu Ser Gly Ile Val Gly Met Leu
1               5

<210> SEQ ID NO 45
<211> LENGTH: 10
```

<212> TYPE: PRT
<213> ORGANISM: artificial sequence
<220> FEATURE:
<223> OTHER INFORMATION: synthetic

<400> SEQUENCE: 45

Phe Leu Ser Gly Ile Val Gly Met Leu Ala
1               5                   10

<210> SEQ ID NO 46
<211> LENGTH: 10
<212> TYPE: PRT
<213> ORGANISM: artificial sequence
<220> FEATURE:
<223> OTHER INFORMATION: synthetic

<400> SEQUENCE: 46

Phe Leu Ser Gly Ile Val Gly Met Leu Ala
1               5                   10

<210> SEQ ID NO 47
<211> LENGTH: 12
<212> TYPE: PRT
<213> ORGANISM: artificial sequence
<220> FEATURE:
<223> OTHER INFORMATION: synthetic

<400> SEQUENCE: 47

Phe Leu Ser Gly Ile Val Gly Met Leu Ala Lys Leu
1               5                   10

<210> SEQ ID NO 48
<211> LENGTH: 13
<212> TYPE: PRT
<213> ORGANISM: artificial sequence
<220> FEATURE:
<223> OTHER INFORMATION: synthetic

<400> SEQUENCE: 48

Phe Leu Ser Gly Ile Val Gly Met Leu Ala Lys Leu Phe
1               5                   10

<210> SEQ ID NO 49
<211> LENGTH: 11
<212> TYPE: PRT
<213> ORGANISM: artificial sequence
<220> FEATURE:
<223> OTHER INFORMATION: synthetic

<400> SEQUENCE: 49

Ser Ala Ile Val Ala Met Leu Gly Lys Leu Phe
1               5                   10

<210> SEQ ID NO 50
<211> LENGTH: 10
<212> TYPE: PRT
<213> ORGANISM: artificial sequence
<220> FEATURE:
<223> OTHER INFORMATION: synthetic

<400> SEQUENCE: 50

Ala Ile Val Ala Met Leu Gly Lys Leu Phe
1               5                   10

<210> SEQ ID NO 51
<211> LENGTH: 9
<212> TYPE: PRT

```
<213> ORGANISM: artificial sequence
<220> FEATURE:
<223> OTHER INFORMATION: synthetic

<400> SEQUENCE: 51

Ile Val Ala Met Leu Gly Lys Leu Phe
1               5

<210> SEQ ID NO 52
<211> LENGTH: 8
<212> TYPE: PRT
<213> ORGANISM: artificial sequence
<220> FEATURE:
<223> OTHER INFORMATION: synthetic

<400> SEQUENCE: 52

Val Ala Met Leu Gly Lys Leu Phe
1               5

<210> SEQ ID NO 53
<211> LENGTH: 7
<212> TYPE: PRT
<213> ORGANISM: artificial sequence
<220> FEATURE:
<223> OTHER INFORMATION: synthetic

<400> SEQUENCE: 53

Ala Met Leu Gly Lys Leu Phe
1               5

<210> SEQ ID NO 54
<211> LENGTH: 6
<212> TYPE: PRT
<213> ORGANISM: artificial sequence
<220> FEATURE:
<223> OTHER INFORMATION: synthetic

<400> SEQUENCE: 54

Phe Leu Ser Ala Ile Val
1               5

<210> SEQ ID NO 55
<211> LENGTH: 6
<212> TYPE: PRT
<213> ORGANISM: artificial sequence
<220> FEATURE:
<223> OTHER INFORMATION: synthetic

<400> SEQUENCE: 55

Phe Leu Ser Ala Ile Val
1               5

<210> SEQ ID NO 56
<211> LENGTH: 6
<212> TYPE: PRT
<213> ORGANISM: artificial sequence
<220> FEATURE:
<223> OTHER INFORMATION: synthetic

<400> SEQUENCE: 56

Met Leu Gly Lys Leu Phe
1               5

<210> SEQ ID NO 57
<211> LENGTH: 8
<212> TYPE: PRT
<213> ORGANISM: artificial sequence
```

```
<220> FEATURE:
<223> OTHER INFORMATION: synthetic

<400> SEQUENCE: 57

Phe Leu Ser Ala Ile Val Ala Met
1               5

<210> SEQ ID NO 58
<211> LENGTH: 5
<212> TYPE: PRT
<213> ORGANISM: artificial sequence
<220> FEATURE:
<223> OTHER INFORMATION: synthetic

<400> SEQUENCE: 58

Leu Gly Lys Leu Phe
1               5

<210> SEQ ID NO 59
<211> LENGTH: 9
<212> TYPE: PRT
<213> ORGANISM: artificial sequence
<220> FEATURE:
<223> OTHER INFORMATION: synthetic

<400> SEQUENCE: 59

Phe Leu Ser Ala Ile Val Ala Met Leu
1               5

<210> SEQ ID NO 60
<211> LENGTH: 10
<212> TYPE: PRT
<213> ORGANISM: artificial sequence
<220> FEATURE:
<223> OTHER INFORMATION: synthetic

<400> SEQUENCE: 60

Phe Leu Ser Ala Ile Val Ala Met Leu Gly
1               5                   10

<210> SEQ ID NO 61
<211> LENGTH: 12
<212> TYPE: PRT
<213> ORGANISM: artificial sequence
<220> FEATURE:
<223> OTHER INFORMATION: synthetic

<400> SEQUENCE: 61

Phe Leu Ser Ala Ile Val Ala Met Leu Gly Lys Leu
1               5                   10

<210> SEQ ID NO 62
<211> LENGTH: 13
<212> TYPE: PRT
<213> ORGANISM: artificial sequence
<220> FEATURE:
<223> OTHER INFORMATION: synthetic

<400> SEQUENCE: 62

Phe Leu Ser Ala Ile Val Ala Met Leu Gly Lys Leu Phe
1               5                   10

<210> SEQ ID NO 63
<211> LENGTH: 10
<212> TYPE: PRT
<213> ORGANISM: artificial sequence
<220> FEATURE:
```

<223> OTHER INFORMATION: synthetic

<400> SEQUENCE: 63

Ala Ile Val Ala Met Leu Ala Lys Leu Phe
1               5                   10

<210> SEQ ID NO 64
<211> LENGTH: 8
<212> TYPE: PRT
<213> ORGANISM: artificial sequence
<220> FEATURE:
<223> OTHER INFORMATION: artificial

<400> SEQUENCE: 64

Val Ala Met Leu Ala Lys Leu Phe
1               5

<210> SEQ ID NO 65
<211> LENGTH: 7
<212> TYPE: PRT
<213> ORGANISM: artificial sequence
<220> FEATURE:
<223> OTHER INFORMATION: synthetic

<400> SEQUENCE: 65

Ala Met Leu Ala Lys Leu Phe
1               5

<210> SEQ ID NO 66
<211> LENGTH: 7
<212> TYPE: PRT
<213> ORGANISM: artificial sequence
<220> FEATURE:
<223> OTHER INFORMATION: synthetic

<400> SEQUENCE: 66

Phe Leu Ser Ala Ile Val Ala
1               5

<210> SEQ ID NO 67
<211> LENGTH: 6
<212> TYPE: PRT
<213> ORGANISM: artificial sequence
<220> FEATURE:
<223> OTHER INFORMATION: synthetic

<400> SEQUENCE: 67

Met Leu Ala Lys Leu Phe
1               5

<210> SEQ ID NO 68
<211> LENGTH: 5
<212> TYPE: PRT
<213> ORGANISM: artificial sequence
<220> FEATURE:
<223> OTHER INFORMATION: synthetic

<400> SEQUENCE: 68

Leu Ala Lys Leu Phe
1               5

<210> SEQ ID NO 69
<211> LENGTH: 9
<212> TYPE: PRT
<213> ORGANISM: artificial sequence
<220> FEATURE:
<223> OTHER INFORMATION: synthetic

```
<400> SEQUENCE: 69

Phe Leu Ser Ala Ile Val Ala Met Leu
1               5

<210> SEQ ID NO 70
<211> LENGTH: 4
<212> TYPE: PRT
<213> ORGANISM: artificial sequence
<220> FEATURE:
<223> OTHER INFORMATION: synthetic

<400> SEQUENCE: 70

Ala Lys Leu Phe
1

<210> SEQ ID NO 71
<211> LENGTH: 10
<212> TYPE: PRT
<213> ORGANISM: artificial sequence
<220> FEATURE:
<223> OTHER INFORMATION: synthetic

<400> SEQUENCE: 71

Phe Leu Ser Ala Ile Val Ala Met Leu Ala
1               5                   10

<210> SEQ ID NO 72

<400> SEQUENCE: 72

000

<210> SEQ ID NO 73
<211> LENGTH: 10
<212> TYPE: PRT
<213> ORGANISM: artificial sequence
<220> FEATURE:
<223> OTHER INFORMATION: synthetic

<400> SEQUENCE: 73

Phe Leu Ser Ala Ile Val Ala Met Leu Ala
1               5                   10

<210> SEQ ID NO 74
<211> LENGTH: 11
<212> TYPE: PRT
<213> ORGANISM: artificial sequence
<220> FEATURE:
<223> OTHER INFORMATION: synthetic

<400> SEQUENCE: 74

Phe Leu Ser Ala Ile Val Ala Met Leu Ala Lys
1               5                   10

<210> SEQ ID NO 75
<211> LENGTH: 12
<212> TYPE: PRT
<213> ORGANISM: artificial sequence
<220> FEATURE:
<223> OTHER INFORMATION: synthetic

<400> SEQUENCE: 75

Phe Leu Ser Ala Ile Val Ala Met Leu Ala Lys Leu
1               5                   10
```

```
<210> SEQ ID NO 76
<211> LENGTH: 13
<212> TYPE: PRT
<213> ORGANISM: artificial sequence
<220> FEATURE:
<223> OTHER INFORMATION: synthetic

<400> SEQUENCE: 76

Phe Leu Ser Ala Ile Val Ala Met Leu Ala Lys Leu Phe
1               5                   10
```

ANTICANCER PEPTIDES

BACKGROUND OF THE INVENTION

Cancer refers to abnormal and uncontrolled cell growth and is one of the main causes of mortality worldwide. Conventional treatments comprises chemotherapy or radiation with lack of selectivity for cancer cells, causing deleterious damage to healthy cells and tissues due to their indiscriminating action, toxicity towards vital organs and severe inflammatory response due to necrosis.

Selectivity of therapeutic agents towards cancerous cells can be improved by conjugating the anticancer drugs with specific cancer targeting ligand such as tumor targeting peptides, antibodies.

Breast cancer accounts for one of the major causes of death in women. Chemotherapy, radiation, and hormonal therapy used to treat breast cancer, are all associated with severe side effects and lack tumor targeting specificity.

Some decapeptides (SEQ ID NO: 9: WLEAAYQKFL), with different residues at X positions have been found to have specific affinity to breast cancer cell lines. One of these peptide analogs conjugated with standard anticancer drug doxorubicin induced the selective effect against breast cancer than standard drug alone.

Temporins are antimicrobial peptides having 10 to 14 amino acids, isolated from skin secretions of amphibians. The temporin SHa (SEQ ID NO: 1: F-L-S-G-I-V-G-M-L-G-K-L-F) was identified as a potent inhibitor of bacteria, yeasts, fungi, and protozoa, as well as antiparasitic activity against promastigote and the intracellular stage (amastigote) of *Leishmania infantum*. Lysine-substituted analogs of temporin SHa such as [$K^3$] temporin-SHa showed more potent antimicrobial activity than temporin-SHa, while L-alanine substituted analogs lack the antibacterial and antiparasitic activity. According to literature report, [$K^3$] temporin-SHa and temporin-SHa exhibited low cytotoxicity (human erythrocytes, THP-1 monocytes and THP-1-derived macrophages) or no cytotoxicity (HepG2 cells and fibroblasts). While, L-alanine substituted analogs [$A^{2,6,9}$] SHa and [$A^{2,6,9}$, $K^3$] SHa were inactive on THP-1 monocytes and HepG2 cells.

Antimicrobial peptides such as temporin-10Ea also demonstrated anticancer activities. Previous studies reported necrosis as a mode of cell death induced by some antimicrobial peptides, caused by the direct interaction of peptides to the plasma membrane resulting in the production of reactive oxygen species, leakage of calcium ions and rapid decrease in mitochondrial membrane production.

In order to meet with the demand of developing new and selective anticancer drugs with no adverse effects on other vital organs or tissues, we developed five new anticancer D-alanine substituted analogs (SEQ ID NOs 2-6) of temporin-SHa along with two anticancer peptide conjugates. The conjugate 7 was developed by linking a new anticancer analog (SEQ ID NO: 4) with a breast cancer targeting peptide, while conjugate 8 was obtained by conjugating the dimeric form of SEQ ID NO: 4 with cancer targeting ligand.

BRIEF SUMMARY OF THE INVENTION

In the current study, anticancer screening of natural product temporin-SHa (SEQ ID NO: 1) and five new analogs (SEQ ID NOs: 2-6) was performed against different cancer cell lines which revealed the anticancer activities of new analogs of temporin SHa. The new analog SEQ ID NO: 4 was identified as cytotoxic ($IC_{50}$ between 16-24 µM) against MCF-7, HeLa, H460, and 3T3 cell lines. The peptide SEQ ID NO: 4 was further conjugated at its Lys residue with breast cancer targeting peptide (SEQ ID NO. 9: WLEAAYQKFL), to produce conjugate 7 which was found to have targeted action on MCF-7 with no cytotoxicity to normal 3T3 cell lines and to any other cancer cell lines used in this study. Due its specific action on breast cancer cells (MCF-7), detailed mechanistic studies were performed on conjugate 7 to investigate its mode of action on MCF-cell line.

The tunnel assay indicated that SEQ ID NO: 4 was necrotic, while conjugate 7 after ligand conjugation with SEQ ID NO: 4 at its Lys residue, caused the apoptosis as evidenced by high levels of DNA fragmentation. To validate apoptotic activity of conjugate 7 further, the effect of the conjugate 7 was studied on the expression levels of pro- and anti-apoptotic genes i.e., Bcl-2, Bax, survivin, and caspase-3 through RT-PCR and immunocytochemistry. The conjugate 7 down-regulated the mRNA expression of Bcl-2 significantly in MCF-7 cells, up-regulated Bax gene expression at post-transcription levels and decreased survivin mRNA quantity in MCF-7 cells which plays its part in programmed cell death at transcriptional and translational levels. Conjugate 7 caused the induction of apoptosis in MCF-7 cells tested through the up-regulation of caspase-3 expression as evidenced by the increase in mRNA levels that was from 4 to 6 folds at different doses. This up-regulation confirmed the induction of apoptosis due to inhibition in expression of anti-apoptotic type of genes i.e. Bcl-2 family.

Peptide conjugate 8 was developed by conjugating the cancer targeting ligand (SEQ ID NO. 7: WLEAAYQKFL) with dimeric form of anticancer peptide SEQ ID NO: 4 through lysine linker. Conjugate 8 was more active against MCF-7 ($IC_{50}$ 1.7 µM) than SEQ ID NO: 4 as well as conjugate 7 and it was as active as standard anticancer drug doxorubicin with no cytotoxicity to 3T3 murine fibroblast cell line.

One-way ANOVA was used for significant difference (i.e. *p<0.05, p<0.01 and *p<0.001) in comparison with control cells.

Figure 4:
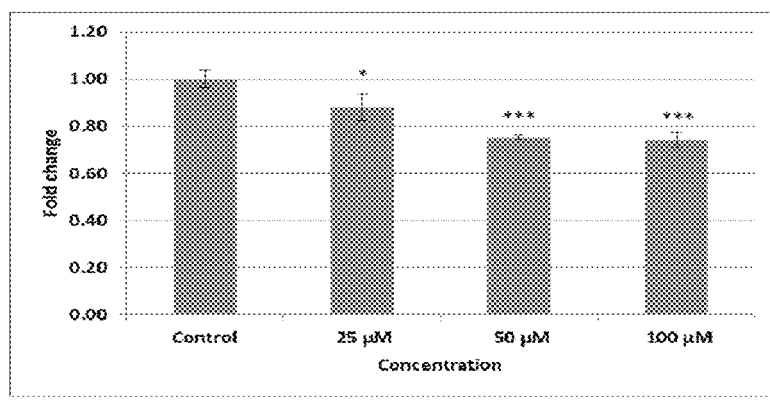

FIG. 4 depicts Bax gene expression in treated MCF-7 cells. RT-PCR was performed for Bax gene in triplicate for all doses and data was normalized using GAPDH. Cells incubated with complete medium only are represented by the bar labeled as Control. Data represents the mean of triplicates ±Standard deviation. One-way ANOVA was used for significant difference (i.e. * denotes p-value less 0.05,  denotes p-value less 0.01 and * denotes p-value less 0.001) when comparing treated samples with control cells.

Figure 5:
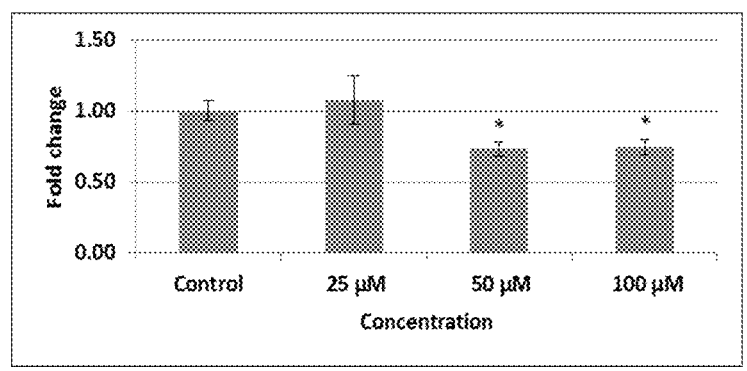

FIG. 5 depicts gene expression analysis of survivin in MCF-7 cells. Real time PCR was performed in triplicate for each dose and data normalization was done with GAPDH as a housekeeping gene. Bar labeled as control represents untreated control cells incubated in complete medium. Data are represented as a mean of triplicates ±Standard deviation. One-way ANOVA was used for significant difference (i.e. *p<0.05, p<0.01 and *p<0.001) in comparison to control cells.

Figure 6:
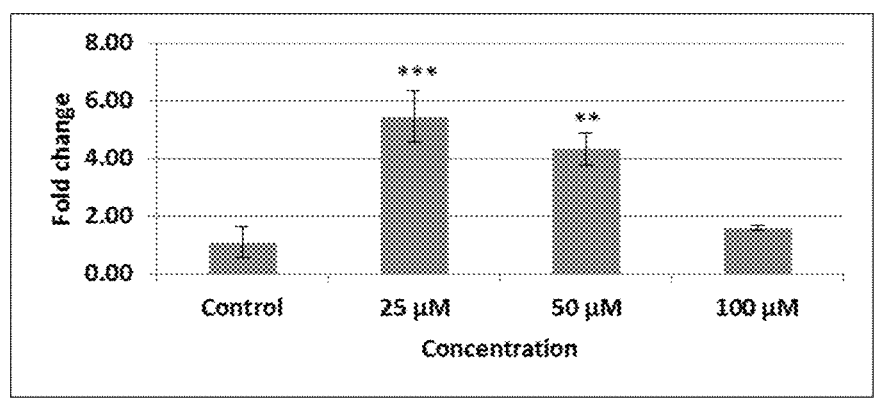

FIG. 6 depicts gene expression analysis of caspase-3 in MCF-7 cells. Data are represented as a mean of triplicates ±standard deviation. One-way ANOVA was used for significant difference (i.e. *p<0.05, p<0.01 and *p<0.001) in comparison with control cells.

Figure 7A:
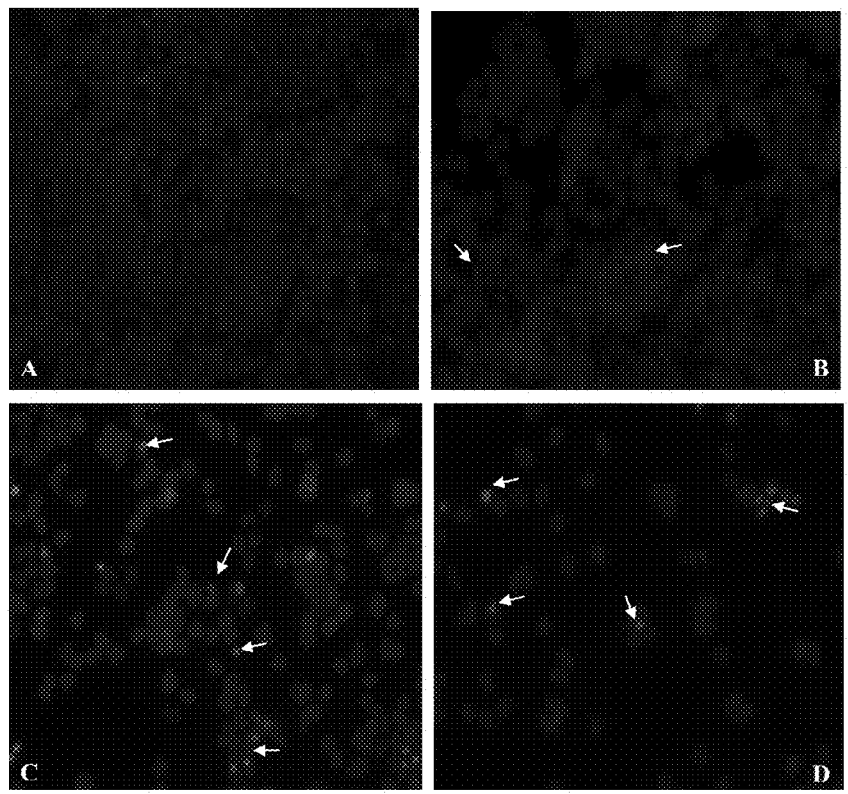

FIG. 7A depicts nuclear staining of MCF-7 cells with DAPI. (A) Control cells; (B) Cells treated with 25 µM of conjugate 7; (C) with 50 µM of conjugate 7 and (D) with 100 µM of conjugate 7. Treated cells were then fixed and incubated with DAPI and images taken under Nikon 90i microscope. Arrow heads are indicating the condensation of nuclear material and/or formation of apoptotic bodies in the treated images.

Figure 7B:
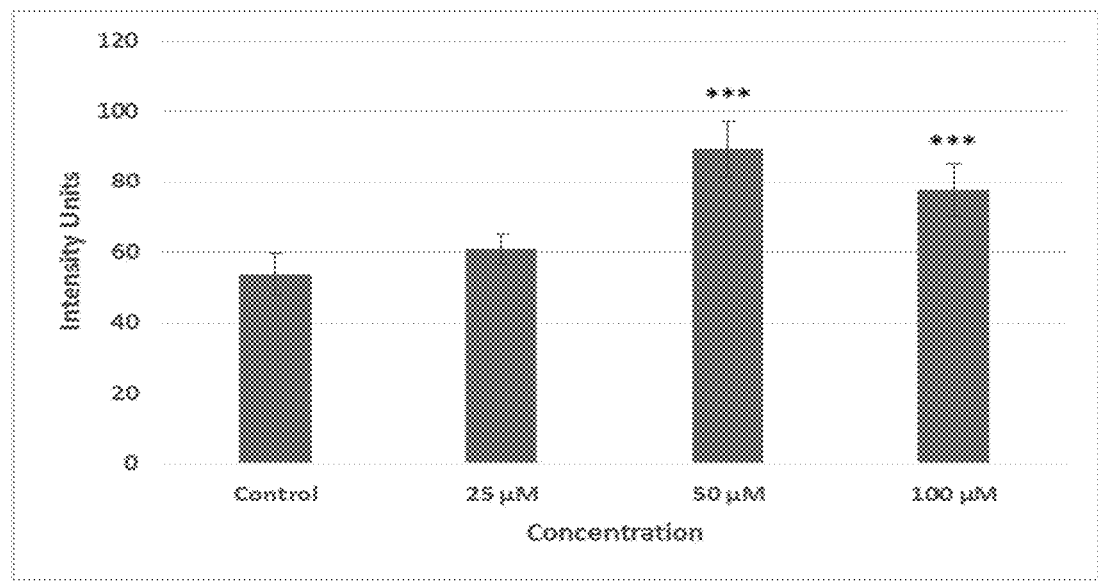

FIG. 7B indicates the arbitrary intensity units for their respective micrographs quantified with the help of ImageJ software.

Figure 8A:
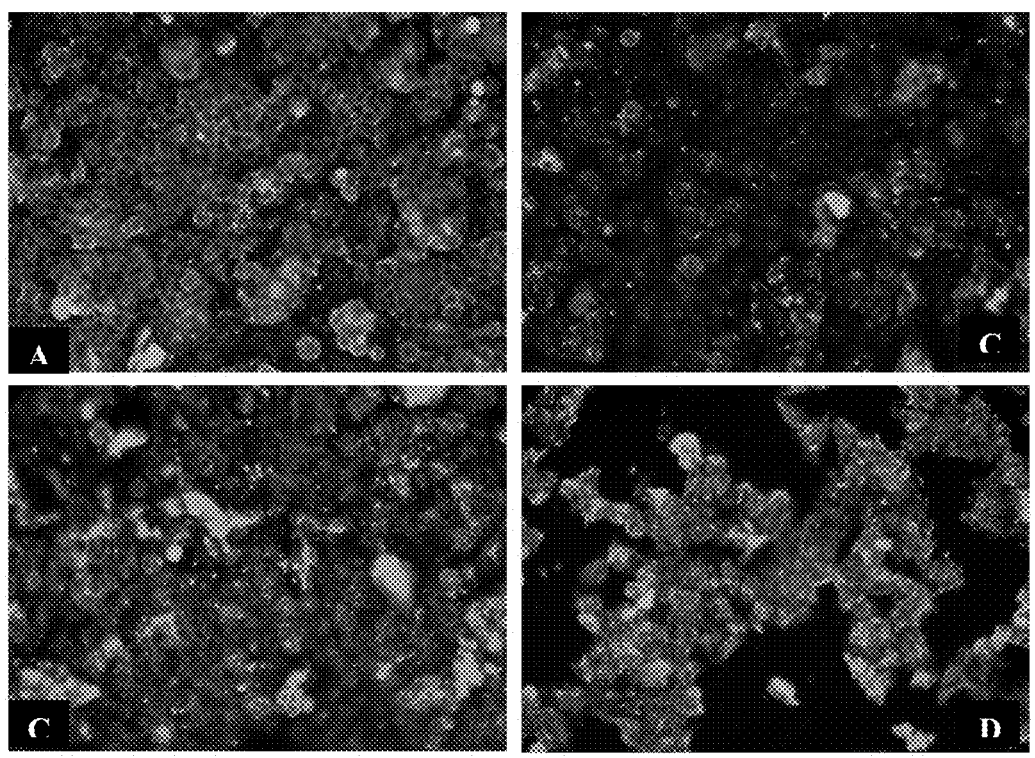

FIG. 8A depicts immunocytochemistry of MCF-7 cells for β-actin expression. Immunostaining was performed after treatment with medium only (A); with 25 µM (B); with 50 µM (C) and with 100 µM of conjugate 7 (D). Treated cells were then fixed and incubated with anti-human β-actin primary antibody produced in mouse, then with FITC-labelled goat secondary antibody.

Figure 8B:
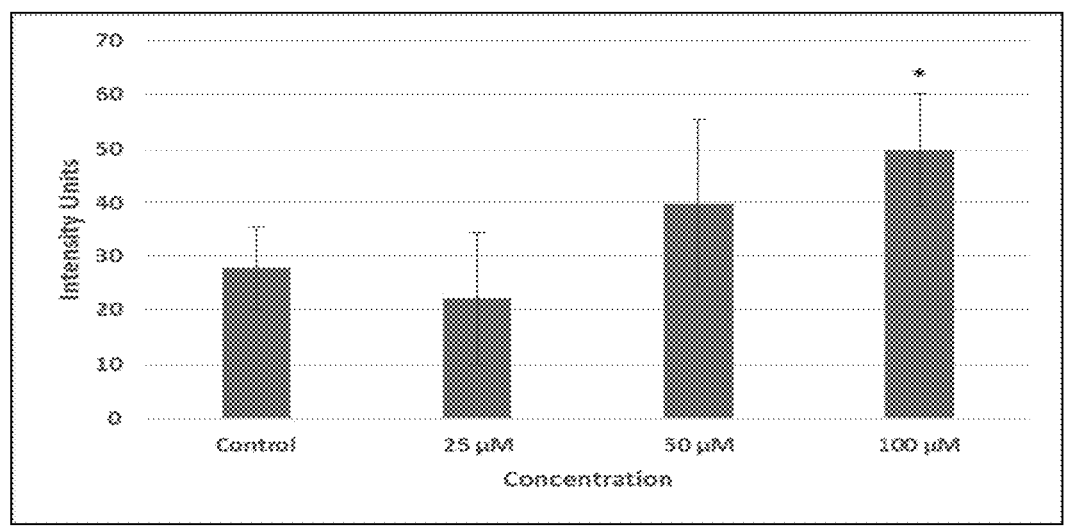

FIG. 8B indicates the arbitrary intensity units for their respective micrographs quantified with the help of ImageJ software.

Figure 9A:
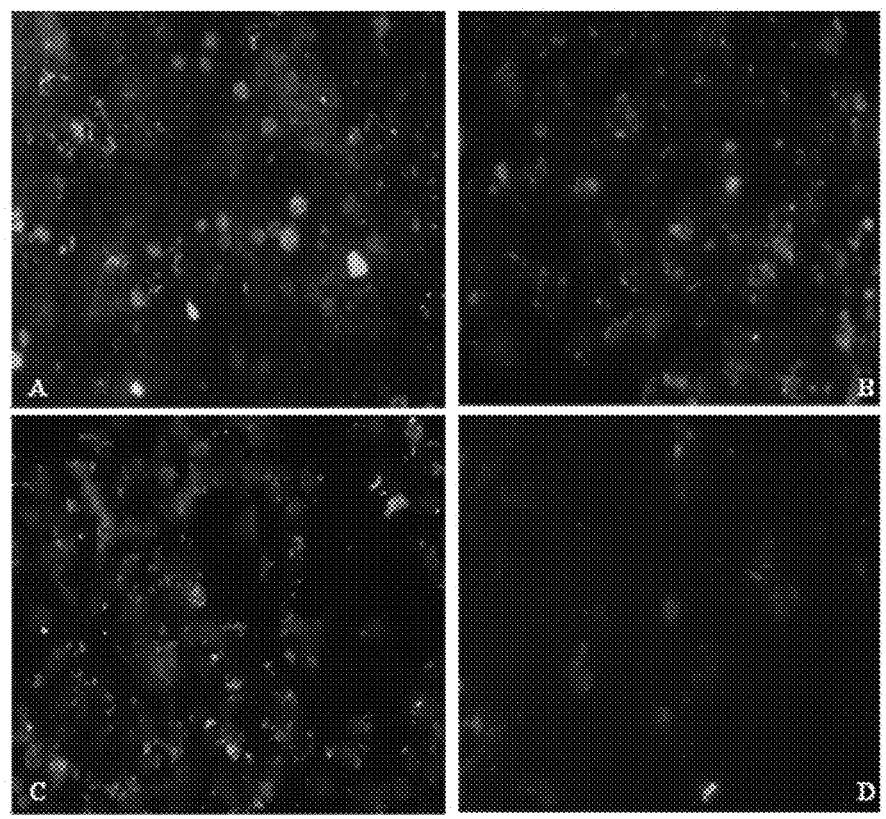

FIG. 9A depicts immunocytochemistry of MCF-7 cells for Bcl-2 expression. Immunostaining was performed after treatment with medium only (A); with 25 µM (B); with 50 µM (C) and with 100 µM of conjugate 7 (D). Treated cells were then fixed and incubated with anti-human Bcl-2 primary antibody produced in mouse, then with FITC-labelled goat secondary antibody.

Figure 9B:
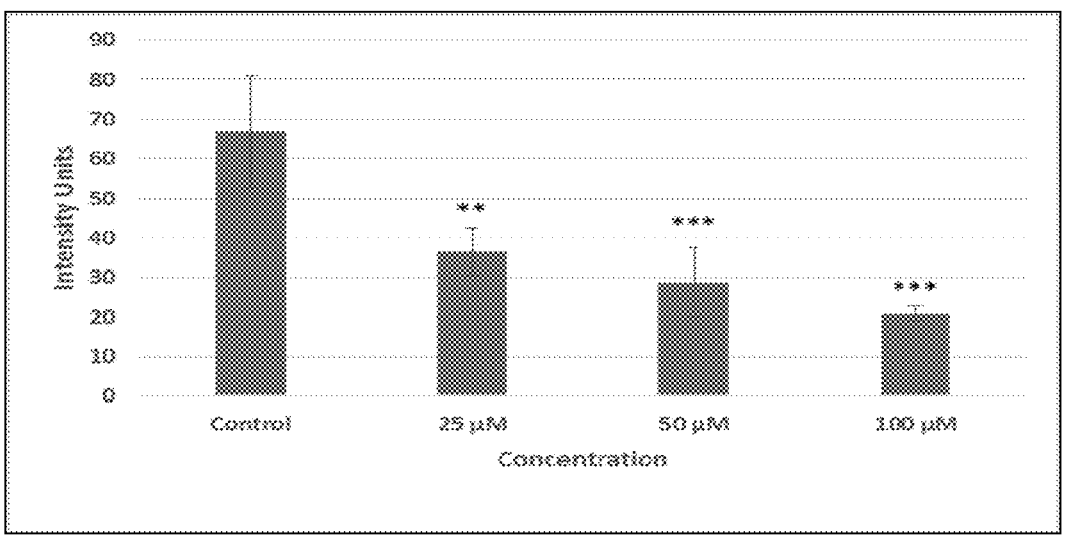

FIG. 9B indicates the arbitrary intensity units for their respective micrographs quantified with the help of ImageJ software.

Figure 10A:
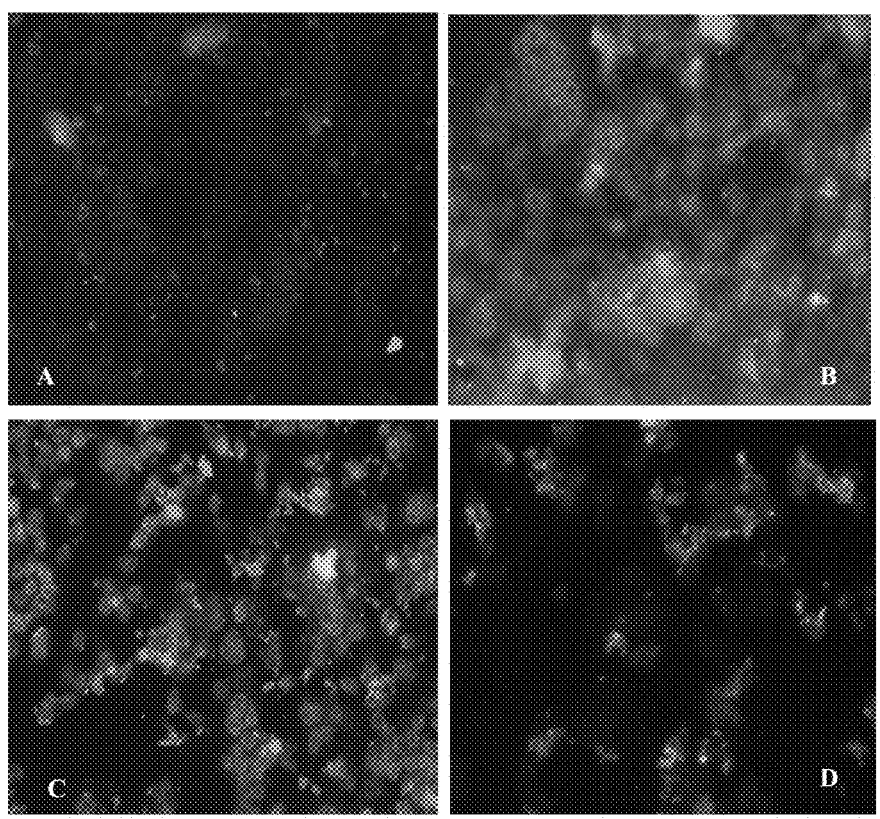

FIG. 10A depicts immunocytochemistry of MCF-7 cells for Bax expression. Immunostaining was performed after treatment with medium only (A); with 25 µM (B); with 50 µM (C) and with 100 µM of conjugate 7 (D). Treated cells were then fixed and incubated with anti-human Bax primary antibody produced in mouse, then with FITC-labeled goat secondary antibody.

Figure 10B:
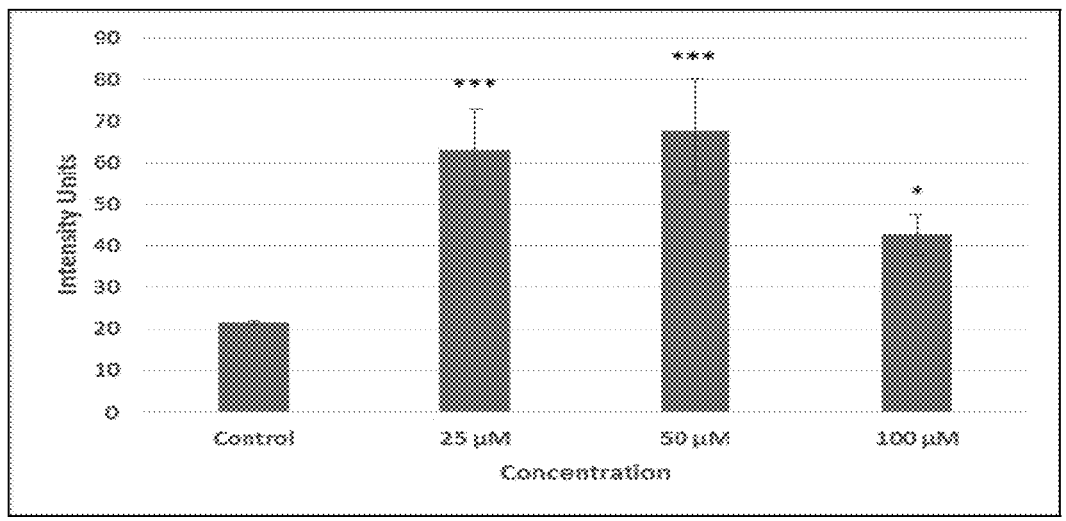

FIG. 10B indicates the arbitrary intensity units for their respective micrographs quantified with the help of ImageJ software.

Figure 11A:
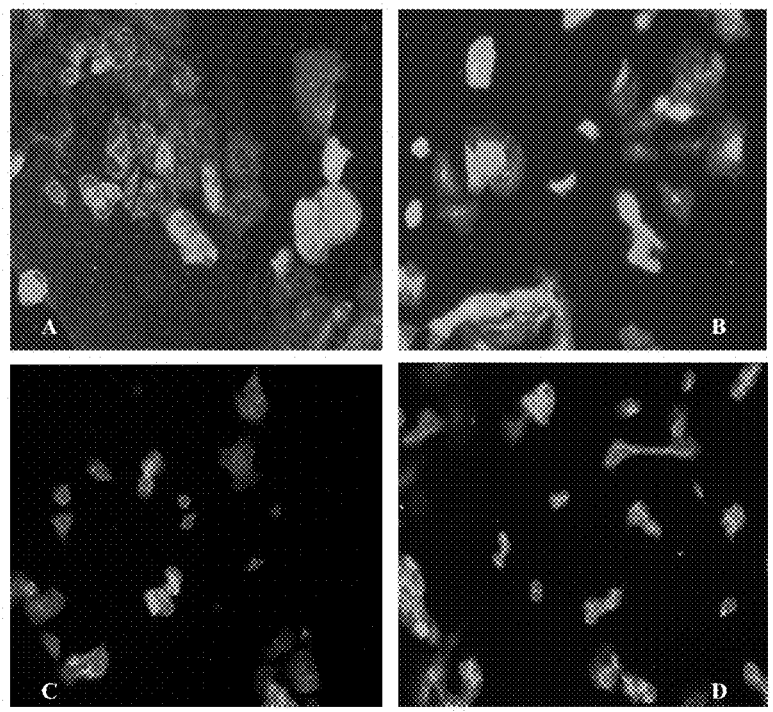

FIG. 11A depicts immunocytochemistry of MCF-7 cells for survivin expression. (A) Control where cells were incubated with medium only; (B) Cells treated with 25 µM of conjugate 7; (C) cells treated with 50 µM of conjugate 7 and (D) cells treated with 100 µM of conjugate 7. Treated cells were then fixed and incubated with anti-human survivin primary antibody produced in mouse, then with goat secondary antibody conjugated with fluorescein isothiocyanate (FITC) and images taken under Nikon 90i Microscope.

Figure 11B:
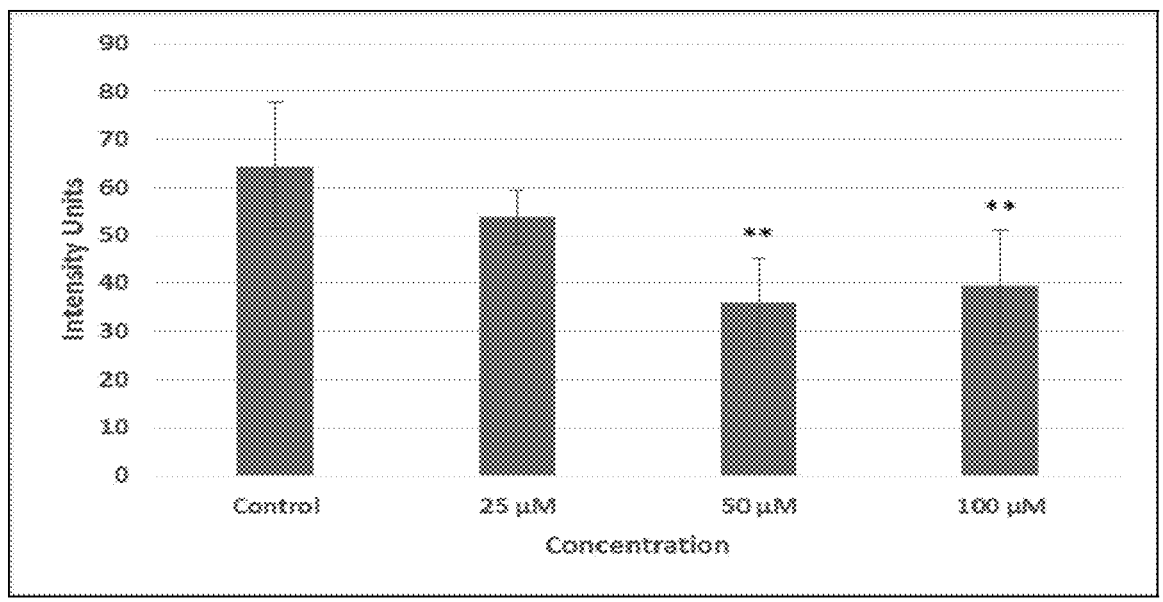

FIG. 11B indicates the arbitrary intensity units for their respective micrographs quantified with the help of ImageJ software.

Figure 12:
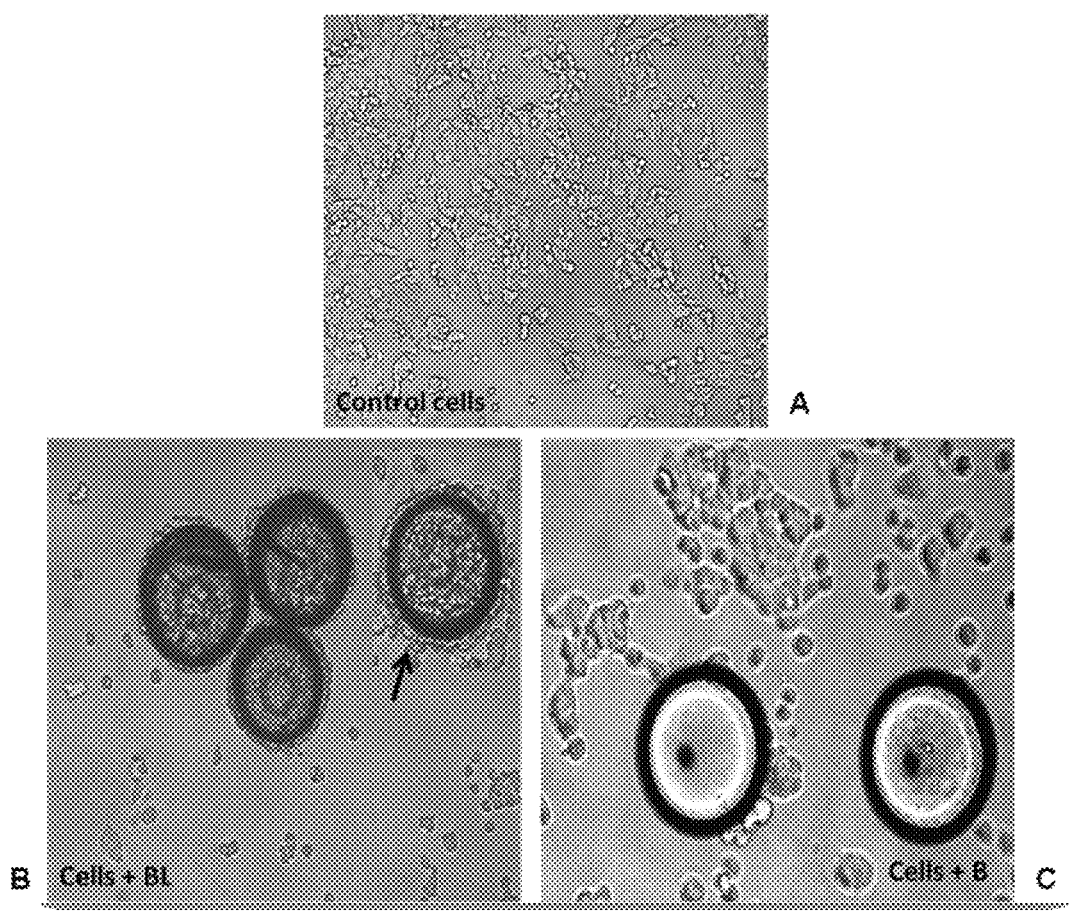

FIG. 12. MCF-7 cells bound to bead containing peptide ligand A.

DETAILED DESCRIPTION OF THE INVENTION

Synthesis.

Temporin-SHa (1) and its analogs ([$K^3$] temporin-SHa are reported antimicrobial peptides, while L-alanine-substituted analogs [$A^{2,6,9}$] temporin-SHa, [$A^{2,6,9}$, $K^3$] temporin-SHa lack the antibacterial and antiparasitic activity. To-date no anticancer activity of temporin-SHa (1) and any of its analog is reported.

Figure 1:
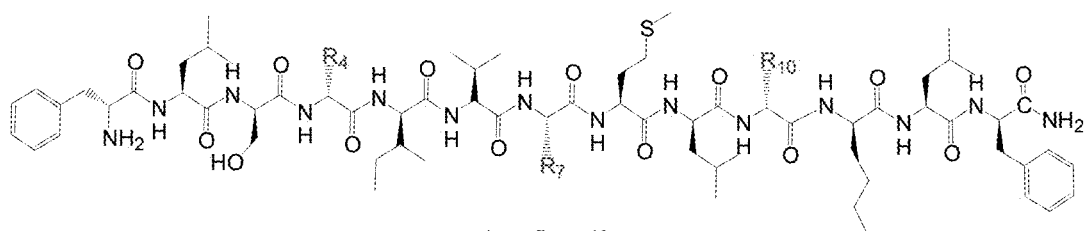
FIG. 1 depicts structures of peptides 1-8.
Figure 1:
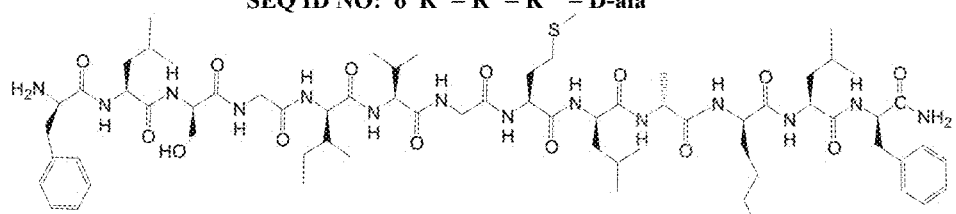
Figure 1:
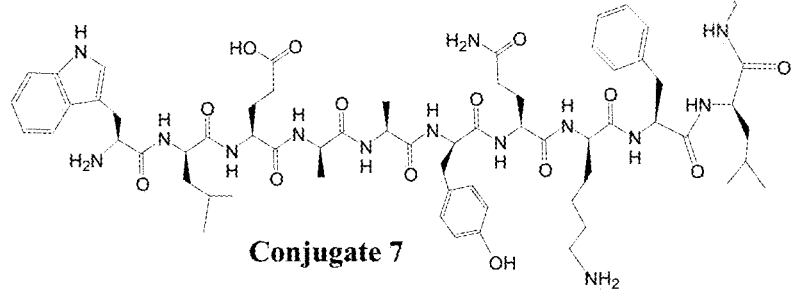
Figure 1:
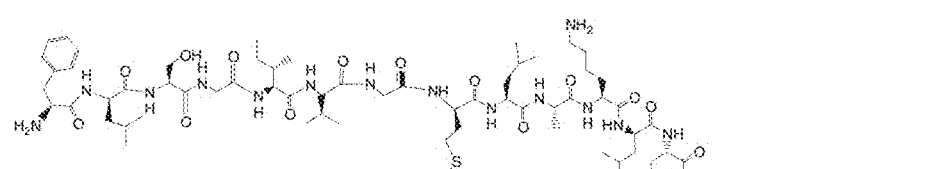
Figure 1:
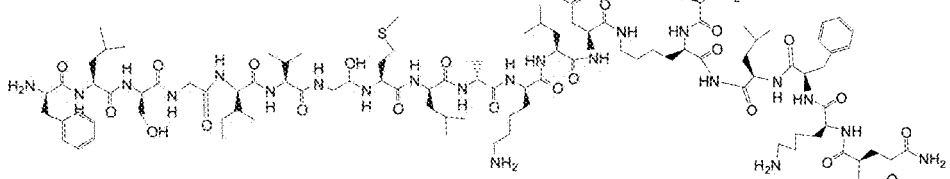
Figure 1:
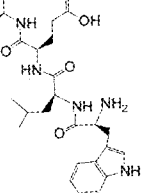

Partial or entire D-amino acid substitution is reported as highly useful approach to develop better therapeutic activities, to increase the resistance to proteolysis and to overcome many hurdles faced by host defense peptides. In the current study, more flexible achiral glycine residues at position 4, 7 and 10 of SEQ ID NO 1 (Temporin SHa) were substituted with ala, and the new substituted analogs SEQ ID NO: 2, SEQ ID NO: 3 and SEQ ID NO: 4, SEQ ID NO: 5, SEQ ID NO: 6 (FIG. 1) were synthesized by Fmoc synthesis protocol The new peptides were characterized by FIRMS (Table 1) MALDI/MS/MS (Table 2), and NMR studies.

TABLE 1

Characterization Data of peptides 1-8

| No. | SEQ. ID NO.* | Obs. mass | HRMS | % yield |
|---|---|---|---|---|
| 1 | F-L-S-G-I-V-G-M-L-G-K-L-F | [M + Na]$^+$ 1402.8 | 1402.7891 | 37.0 |
| 2 | F-L-S-a-I-V-G-M-L-G-K-L-F | [M + Na]$^+$ 1416.8 | 1416.8048 | 68.57 |

TABLE 1-continued

Characterization Data of peptides 1-8

| No. | SEQ. ID NO.* | Obs. mass | HRMS | % yield |
|---|---|---|---|---|
| 3 | F-L-S-G-I-V-a-M-L-G-K-L-F | $[M + Na]^+$ 1416.9 | 1416.8084 | 69.62 |
| 4 | F-L-S-G-I-V-G-M-L-a-K-L-F | $[M + H]^+$ 1394.9 | 1394.8228 | 81.68 |
| 5 | F-L-S-a-I-V-a-M-L-G-K-L-F | $[M + Na]^+$ 1430.8 | 1430.8204 | 80.29 |
| 6 | F-L-S-a-I-V-a-M-L-a-K-L-F | $[M + Na]^+$ 1444.8 | 1444.8361 | 27.93 |
| 7 (CONJUGATE 7) | F-L-S-G-I-V-G-M-L-a-K-L-F<br>\|<br>W-L-E-A-A-Y-Q-K-F-L | $[M + Na]^+$ 2666.5 | 2666.4543 | 13.1 |
| 8 (CONJUGATE 8) | F-L-S-G-I-V-G-M-L-a-K-L-F-K<br>\|<br>F-L-S-G-I-V-G-M-L-a-K-L-F-K<br>\|<br>W-L-E-A-A-Y-Q-K-F-L | $[M + Na]^+$ 4299.99 | — | 14.9 |

*Lower case letter "a" denotes D-alanine

Anticancer screening results showed that the temporin SHa (1) was active against MCF-7, HeLa, and H460 cell lines with no cytotoxicity against DoHH2 cell line. The SEQ ID NO: 1 was also previously reported as non-cytotoxic against HepG2 cell line. The SEQ ID NO: 4 containing D-alanine in place of glycine at position 10 of natural peptide, was cytotoxic against MCF-7, HeLa, H460 and 3T3 murine fibroblast cell lines. While peptides containing D-alanine in place of glycine at positions 4 (SEQ ID NO: 2), position 7 (SEQ ID NO: 3) and positions 4, 7, 10 (SEQ ID NO: 6) were found to be selectively active against MCF-7 cell line with no cytotoxicity against any cancer cell lines used in this study and also inactive against 3T3 cell line. On the other hand, SEQ ID NO: 5 containing glycine replaced by D-alanine at position 4 and 7, was active against MCF-7 and H460 cell lines with no cytotoxicity against 3T3 murine fibroblast cell line. None of these peptides showed activity against B-cell lymphoma (DoHH2 cell line).

In the synthesis of conjugate 7, the Lys residue of SEQ ID NO: 4 was conjugated with breast cancer targeting peptide A (SEQ ID NO: 7: WLEAAYQKFL). The peptide ligand A was different from previously reported breast cancer targeting decapeptide 18-4a having $K^8$ and $L^2$ in place of $k^8$ and $Nle^2$, respectively. The peptide A also showed strong binding to MCF-7 cells in cell-growth on bead assay (FIG. 12). The conjugate 7 derived from targeting of SEQ ID NO: 4 with breast cancer targeting peptide, was found active only against MCF-7 with no cytotoxicity against any other cell line used in this study.

In the synthesis of conjugate 8, the dimeric form of peptide SEQ ID NO: 4 was conjugated with breast cancer targeting peptide A (SEQ ID NO: 7: WLEAAYQKFL) through lysine connected to second K, to produce conjugate 8. Conjugate 8 was highly potent against MCF-7 (1.7 µM) but did not showed cytotoxicity on 3T3 cell line up to the dose of 100 µg/mL. Conjugate 8 has different site of conjugation with cancer targeting ligand than conjugate 7. It also comprises of dimeric form of anticancer SEQ ID NO 4, therefore its potency and selectivity was found different from conjugate 7. It was also active against cervical and lung cancer cell lines.

TABLE 2

Cytotoxicity Studies of Peptides 1-8 ($IC_{50}$ in µM).

| No. | 3T3 | MCF-7 | HeLa | H460 | DoHH2 |
|---|---|---|---|---|---|
| 1 | 73.3 ± 0.07 | 14.47 ± 0.57 | 18.36 ± 0.92 | 34.49 ± 1.5 | >100 |
| 2 | >100 | 17.9 ± 1.1 | >100 | >100 | >100 |
| 3 | >100 | 22.4 ± 2.2 | >100 | >100 | >100 |
| 4 | 16.02 ± 3.7 | 16.2 ± 2.2 | 22.7 ± 0.86 | 24.3 ± 0.84 | >100 |
| 5 | >100 | 29.5 ± 6.03 | >100 | 37.3 ± 3.5 | >100 |
| 6 | >100 | 26.33 ± 5.8 | >100 | >100 | >100 |
| 7 | >100 | 23.2 ± 2.1 | >100 | >100 | >100 |
| 8 | >100 | 1.7 ± 0.18 | 8.7 ± 0.65 | 14.27 ± 0.7 | >100 |
| Cyclohexamide | 0.46 ± 0.07 | — | — | — | — |
| Doxorubicin | — | 1.6 ± 0.2 | 5.7 ± 0.36 | — | — |
| Cisplatin | — | — | — | 10.3 ± 0.6 | — |
| Imatinib | — | — | — | — | 42.5 ± 3.5 |

TABLE 3

MSAVIS fragments of peptides 2-6

| No. | SEQ ID NO: | MS/MS fragment of [M + Na]+ | Proposed fragment structure |
|---|---|---|---|
| 2 | Phe-Leu-Ser-ala-Ile-Val-Gly-Met-Leu-Gly-Lys-Leu-Phe | 1416.8 | [M + Na]+ |
|   |   | 1069.2 | [H₂N-[SEQ ID NO. 10: ala-Ile-Val-Gly-Met-Leu-Gly-Lys-Leu-Phe]-CO-NH₂]Na+ |
|   |   | 998.2 | [H₂N-[[SEQ ID NO. 11: Ile-Val-Gly-Met-Leu-Gly-Lys-Leu-Phe-CO-NH₂]Na+ |
|   |   | 885.2 | [H₂N-[SEQ ID NO. 12: Val-Gly-Met-Leu-Gly-Lys-Leu-Phe]-CO-NH₂]Na+ |
|   |   | 656.3 | [[SEQ ID NO. 13:-[Phe-Leu-Ser-ala-Ile-Val-CHO]Na+ |
|   |   | 729.3 | [H₂N-[SEQ ID NO. 14: Met-Leu-Gly-Lys-Leu-Phe]-CO-NH₂]Na+ |
|   |   | 813.2 | [[SEQ ID NO. 15: Phe-Leu-Ser-ala-Ile-Val-Gly-Met]]Na+ |
|   |   | 589.4 | [H₂N-[SEQ ID NO. 16: Leu-Gly-Lys-Leu-Phe]-CO-NH₂]Na+ |
|   |   | 926.2 | [[SEQ ID NO. 17: Phe-Leu-Ser-ala-Ile-Val-Gly-Met-Leu]]Na+ |
|   |   | 485.3 | [H₂N-[SEQ ID NO. 18: Gly-Lys-Leu-Phe]-CO-NH₂]Na+ |
|   |   | 1028.2 | [SEQ ID NO. 19: Phe-Leu-Ser-ala-Ile-Val-Gly-Met-Leu-Gly]-CO-NH₂]Na+ |
|   |   | 1156.2 | [[SEQ ID NO. 20: Phe-Leu-Ser-ala-Ile-Val-Gly-Met-Leu-Gly-Lys]-CO-NH₂]Na+ |
|   |   | 1224.2 | [[SEQ ID NO. 21: Phe-Leu-Ser-ala-Ile-Val-Gly-Met-Leu-Gly-Lys-Leu]Na+ |
|   |   | 1371.1 | [SEQ ID NO. 22: Phe-Leu-Ser-ala-Ile-Val-Gly-Met-Leu-Gly-Lys-Leu-Phe]-Na+ |
| 3 | Phe-Leu-Ser-Gly-Ile-Val-ala-Met-Leu-Gly-Lys-Leu-Phe | 1416.7 | [M + Na]+ |
|   |   | 1270.6 | [H₂N-[SEQ ID NO. 23: Leu-Ser-Gly-Ile-Val-Ala-Met-Leu-Gly-Lys-Leu-Phe]-CO-NH₂]Na+ |
|   |   | 1070.7 | [H₂N-[SEQ ID NO. 24: Gly-Ile-Val-Ala-Met-Leu-Gly-Lys-Leu-Phe]-CO-NH₂]Na+ |
|   |   | 1013.6 | [H₂N-[SEQ ID NO. 25: Ile-Val-Ala-Met-Leu-Gly-Lys-Leu-Phe]-CO-NH₂]Na+ |
|   |   | 429.4 | [[SEQ ID NO. 26: Phe-Leu-Ser-Gly]-CHO]Na+ |
|   |   | 900.7 | H₂N-[[SEQ ID NO. 27: Val-Ala-Met-Leu-Gly-Lys-Leu-Phe-CO-NH₂]Na+ |
|   |   | 542.2 | [[SEQ ID NO. 28: Phe-Leu-Ser-Gly-Ile]-CHO]Na+ |
|   |   | 801.6 | [H₂N-[SEQ ID NO. 29: Ala-Met-Leu-Gly-Lys-Leu-Phe-CO-NH₂]Na+ |
|   |   | 683.6 | [[SEQ ID NO. 30: Phe-Leu-Ser-Gly-Ile-Val-Ala]]Na+ |
|   |   | 714.6 | [[SEQ ID NO. 31: Met-Leu-Gly-Lys-Leu-Phe]-CO-NH₂]Na+ |
|   |   | 727.4 | [[SEQ ID NO. 32: Phe-Leu-Ser-Gly-Ile-Val-Ala]-CO-NH₂]Na+ |
|   |   | 599.6 | [H₂N-[SEQ ID NO. 33: Leu-Gly-Lys-Leu-Phe]-CO-NH₂]Na+ |
|   |   | 927.7 | [[SEQ ID NO. 33: Phe-Leu-Ser-Gly-Ile-Val-ala-Met-Leu]]Na+ |
|   |   | 1029.8 | [[SEQ ID NO. 34: Phe-Leu-Ser-Gly-Ile-Val-ala-Met-Leu-Gly]-CO-NH₂]Na+ |
|   |   | 1112.7 | [[SEQ ID NO. 36: Phe-Leu-Ser-Gly-Ile-Val-ala-Met-Leu-Gly-Lys]]Na+ |
|   |   | 1157.7 | [[SEQ ID NO. 37: Phe-Leu-Ser-Gly-Ile-Val-ala-Met-Leu-Gly-Lys]-CO-NH₂]Na+ |
|   |   | 1371.5 | [[SEQ ID NO. 38: Phe-Leu-Ser-Gly-Ile-Val-ala-Met-Leu-Gly-Lys-Leu-Phe-]Na+ |
| 4 | Phe-Leu-Ser-Gly-Ile-Val-Gly7-Met-Leu-ala-Lys-Leu-Phe | 1416.9 | [M + Na]+ |
|   |   | 1157.1 | [H₂N-[SEQ ID NO. 39: Ser-Gly-Ile-Val-Gly-Met-Leu-ala-Lys-Leu-Phe]-CO-NH₂]Na+ |
|   |   | 1070.1 | [H₂N-[SEQ ID NO. 40: Gly-Ile-Val-Gly-Met-Leu-ala-Lys-Leu-Phe]-CO-NH₂]Na+ |
|   |   | 800.1 | [H₂N-[SEQ ID NO. 41: Gly-Met-Leu-ala-Lys-Leu-Phe]-CO-NH₂]Na+ |
|   |   | 744.1 | [H₂N-[SEQ ID NO. 42: Met-Leu-ala-Lys-Leu-Phe]-CO-NH₂]Na+ |
|   |   | 613.1 | [H₂N-[SEQ ID NO. 43: Leu-ala-Lys-Leu-Phe]-CO-NH₂]Na+ |
|   |   | 913.1 | [[SEQ ID NO. 44: Phe-Leu-Ser-Gly-Ile-Val-Gly-Met-Leu]]Na+ |
|   |   | 984.1 | [[SEQ ID NO. 45: Phe-Leu-Ser-Gly-Ile-Val-Gly-Met-Leu-ala]]Na+ |
|   |   | 1029.1 | [[SEQ ID NO. 46: Phe-Leu-Ser-Gly-Ile-Val-Gly-Met-Leu-ala]-CO-NH₂]Na+ |
|   |   | 1225.2[b] | [[SEQ ID NO. 47: Phe-Leu-Ser-Gly-Ile-Val-Gly-Met-Leu-ala-Lys-Leu]]Na+ |
|   |   | 1371.2 | [[SEQ ID NO. 48: Phe-Leu-Ser-Gly-Ile-Val-Gly-Met-Leu-ala-Lys-Leu-Phe-]Na+ |
| 5 | Phe-Leu-Ser-ala-Ile-Val-ala-Met-Leu-Gly-Lys-Leu-Phe | 1430.30 | [M + CO]+ |
|   |   | 1171.2 | [H²N-[SEQ ID NO. 49: Ser-ala-Ile-Val-ala-Met-Leu-Gly-Lys-Leu-Phe]-CO-NH₂]Na+ |
|   |   | 1084.2 | [H₂N-[SEQ ID NO. 50: ala-Ile-Val-ala-Met-Leu-Gly-Lys-Leu-Phe]-CO-NH₂]Na+ |
|   |   | 1013.2 | [H₂N-[SEQ ID NO. 51: Ile-Val-ala-Met-Leu-Gly-Lys-Leu-Phe]-CO-NH₂]Na+ |
|   |   | 900.1 | [H₂N-[SEQ ID NO. 52: Val-ala-Met-Leu-Gly-Lys-Leu-Phe]-CO-NH₂]Na+ |
|   |   | 801.2 | [H₂N-[SEQ ID NO. 53: ala-Met-Leu-Gly-Lys-Leu-Phe]-CO-NH₂]Na+ |
|   |   | 656.3 | [[SEQ ID NO. 54: Phe-Leu-Ser-ala-Ile-Val]]Na+ |
|   |   | 670.4 | [[SEQ ID NO. 55: Phe-Leu-Ser-ala-Ile-Val]-NH₂]Na+ |
|   |   | 730.1 | [H₂N-[SEQ ID NO. 56: Met-Leu-Gly-Lys-Leu-Phe]-CO-NH₂]Na+ |
|   |   | 828.1 | [SEQ ID NO. 57: Phe-Leu-Ser-ala-Ile-Val-ala-Met]Na+ |
|   |   | 599.0 | H₂N-[[SEQ ID NO. 58: Leu-Gly-Lys-Leu-Phe]-CO-NH₂]Na+ |
|   |   | 941.1 | [[SEQ ID NO. 59: Phe-Leu-Ser-ala-Ile-Val-ala-Met-Leu]]Na+ |
|   |   | 1043.3 | [[SEQ ID NO. 60: Phe-Leu-Ser-ala-Ile-Val-ala-Met-Leu-Gly]-CO-NH₂]Na+ |
|   |   | 1239.2 | [[SEQ ID NO. 61: Phe-Leu-Ser-ala-Ile-Val-ala-Met-Leu-Gly-Lys-Leu]]Na+ |
|   |   | 1386.1 | [[SEQ ID NO. 62: Phe-Leu-Ser-ala-Ile-Val-ala-Met-Leu-Gly-Lys-Leu-Phe-]Na+ |

TABLE 3-continued

MSAVIS fragments of peptides 2-6

| No. | SEQ ID NO: | MS/MS fragment of [M + Na]⁺ | Proposed fragment structure |
|---|---|---|---|
| 6 | Phe-Leu-Ser-ala-Ile-Val-ala-Met-Leu-ala-Lys-Leu-Phe | 1444.8 | [M + Na]⁺ |
| | | 1097.9 | [H₂N-[SEQ ID NO. 63: ala-Ile-Val-ala-Met-Leu-ala-Lys-Leu-Phe]-CO-NH₂]Na⁺ |
| | | 913.8 | [H₂N-[SEQ ID NO. 64: Val-ala-Met-Leu-ala-Lys-Leu-Phe]-CO-NH₂]Na⁺ |
| | | 814.8 | [H₂N-[SEQ ID NO. 65: Ala-Met-Leu-ala-Lys-Leu-Phe]-CO-NH₂]Na⁺ |
| | | 696.8 | [[SEQ ID NO. 66: Phe-Leu-Ser-ala-Ile-Val-ala]Na⁺ |
| | | 743.8 | [H₂N-[SEQ ID NO. 67: Met-Leu-ala-Lys-Leu-Phe]-CO-NH₂]Na⁺ |
| | | 612.8 | [H₂N-[SEQ ID NO. 68: Leu-ala-Lys-Leu-Phe]-CO-NH₂]Na⁺ |
| | | 940.8 | [[SEQ ID NO. 69: Phe-Leu-Ser-ala-Ile-Val-ala-Met-Leu]]Na⁺ |
| | | 499.7 | [H₂N-[SEQ ID NO. 70: ala-Lys-Leu-Phe-CO-NH₂]]Na⁺ |
| | | 1011.8 | [[SEQ ID NO. 71: Phe-Leu-Ser-ala-Ile-Val-ala-Met-Leu-ala]]Na⁺ |
| | | 428.7 | H₂N-[[SEQ ID NO. 72: Lys-Leu-Phe-CO-NH₂]]Na⁺ |
| | | 1056.8 | [[SEQ ID NO. 73: Phe-Leu-Ser-ala-Ile-Val-ala-Met-Leu-ala]-CO-NH₂]]Na⁺ |
| | | 1184.9 | [[SEQ ID NO. 74: Phe-Leu-Ser-ala-Ile-Val-ala-Met-Leu-ala-Lys]-CO-NH₂]Na⁺ |
| | | 1252.9 | [[SEQ ID NO. 75: Phe-Leu-Ser-ala-Ile-Val-ala-Met-Leu-ala-Lys-Leu]]Na⁺ |
| | | 1399.9 | [[SEQ ID NO. 76: Phe-Leu-Ser-ala-Ile-Val-ala-Met-Leu-ala-Lys-Leu-Phe]]-Na⁺ |

Studies of Conjugate 7 on MCF-7.

Due to selective action of conjugate 7 on MCF-7 cells, more detailed mechanistic studies were performed on conjugate 7. Furthermore, conjugate 7 was found to be safe against non-cancerous cells as evidenced by MTT assay using mouse fibroblast cell line.

DNA Fragmentation Assay (TUNEL Assay)

Figure 2:
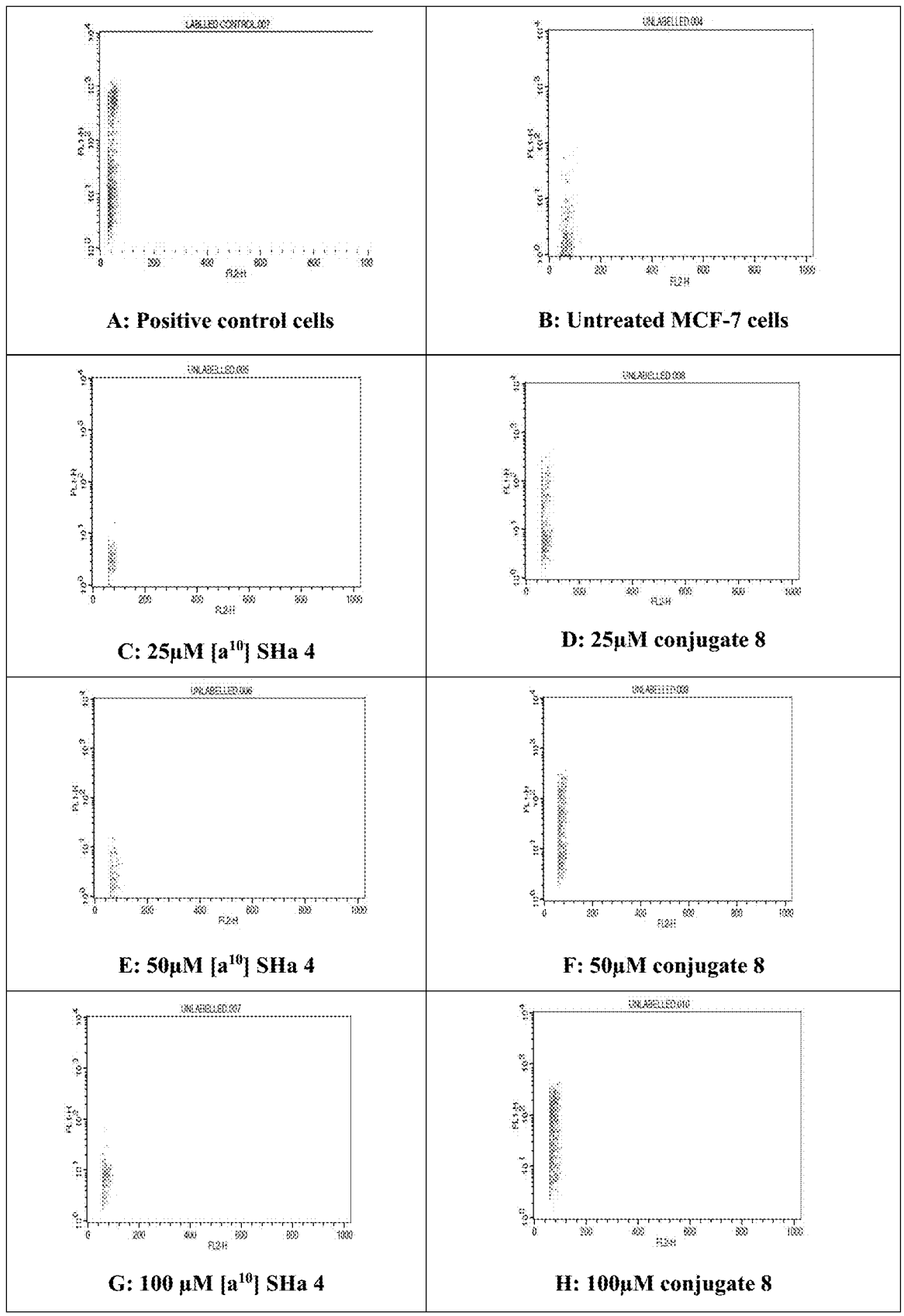
FIG. 2. A depicts TUNEL assay for peptide 4 and conjugate 7 on MCF-7 cells. MCF-7 cells showed necrosis when treated with peptide 4 peptide at different concentrations as shown in boxes C, E and G. On the other hand, conjugate 7 was found to be apoptotic as indicated in boxes D, F and H at different concentrations, nearly showing the same pattern of FITC-fluorescence as reflected by positive apoptotic cells provided by the manufacturer (A). Untreated control cells were incubated with only medium and showed non-apoptotic behavior (B).

Nature of cell death induced by peptides SEQ ID NO: 4 and conjugate 7 was analyzed by DNA fragmentation, through TUNEL assay (kit from Merck) Millipore®. Cultured MCF-7 cells were treated with 0, 25, 50, and 100 µM of SEQ ID NO: 4 and conjugate 7 for 48 hours. Sample preparation was performed according to instructions by manufacturer and analysis was performed on FACSCaliber (BD Biosciences, USA). The SEQ ID NO: 4 treated cells demonstrated extremely low level of DNA fragmentation, as indicated by low fluorescein labeling at all doses (FIGS. 2. C, E and G). However, intense fluorescence signals were achieved for conjugate 7 at 25, 50 and 100 µM, thus indicating highly fragmented DNA (FIGS. 2. D, F and H) and dot plot pattern obtained showed was almost similar as that was obtained in positive control cells (FIG. 2. A). From these observations, it can be concluded that SEQ ID NO: 4 peptide induced cell death via necrosis and conjugate 7 induced programmed type of cell death i.e. apoptosis. From this switching behavior, it is proposed that conjugated ligand help in receptor mediated delivery of peptide SEQ ID NO: 4 or otherwise, inducing apoptosis in cancer cells that could not be achieved without ligand conjugation.

There are few reports that show apoptosis mediated cell death induced by certain antimicrobial peptides. Paredes-Gamero and colleagues (2012) showed that AMPs induced cell death in K562 cells through the activation of caspase-3 dependent apoptosis. Temporin-10Ea is also reported as an activator of cell death in human breast cancer cells through the induction of caspase-dependent pathway at specific doses.

As discussed earlier, SEQ ID NO: 4 induced cell deaths through the process of necrosis before ligand conjugation. Next we checked whether ligand conjugation affected the type of cell death or in other words, mechanism of cell death has been changed from necrosis to apoptosis or remained unaffected. TUNEL assay indicates that SEQ ID NO: 4 after ligand conjugation (conjugate 7) caused the programmed type of cell death as evidenced by high levels of DNA fragmentation (FIG. 2. A). An interesting observation was that the level of apoptosis increased with the increase in dose. These results clearly indicate that SEQ ID NO: 4 peptide that was necrotic without ligand, after conjugation with ligand, causes cell death through the mechanism of apoptosis. The proposed mechanism for this switching of SEQ ID NO: 4 peptide from necrosis to apoptosis after ligand conjugation may include the interaction of cell surface receptor and ligand (conjugated with SEQ ID NO: 4) resulting in the internalization of receptor that delivers the peptide 4 inside the cell and induce apoptosis in them. Another proposed mechanism is the direct internalization of conjugate 7 peptide with the help of hydrophobic part of ligand or by phagocytosis.

Expression of Pro- and Anti-apoptotic Genes Following Treatment with Conjugate 7

The TUNEL Assay clearly indicated that conjugate 7 act as an apoptotic agent; therefore the subsequent studies included the use of conjugate 7 only. Changes in the gene expression of pro and anti-apoptotic gene family proteins i.e. Bcl-2, survivin, and caspase-3 in MCF-7 cell line were evaluated through real time PCR after 24 hour treatment with conjugate 7. For the normalization of gene expression data, GAPDH was taken as house-keeping gene and its expression was checked for each cDNA sample.

Figure 3:
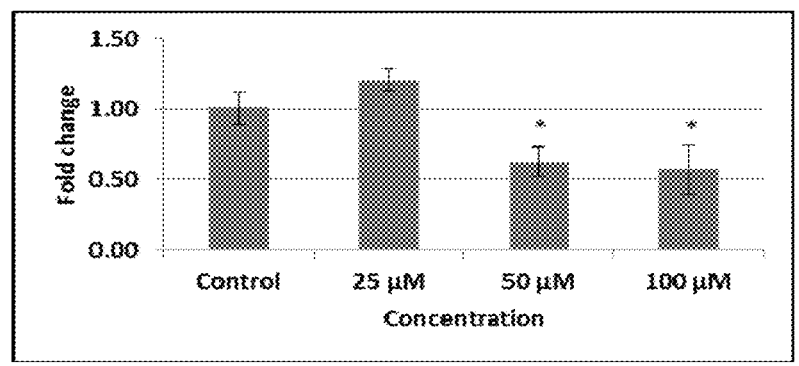
FIG. 3 depicts gene expression analysis of Bcl-2 in MCF-7 cells. Real time PCR was performed in triplicate for each dose and data normalization was done with GAPDH as a house keeping gene. Bar labelled as control represents untreated control cells incubated in complete medium. Data are represented as a mean of triplicates ±Standard deviation.

Apoptosis is a highly regulated phenomenon carried out by different proteins, among them Bcl-2 family proteins are the most important. Bcl-2 family includes pro- and anti-apoptotic proteins that respond to extra- and intra-cellular factors in an excellent co-ordination with each other. Various peptides have been reported for the modulation in gene expression of Bcl-2 protein in cancer cells. A study conducted on bufalin showed significant growth inhibition of ovarian cells through the down-regulation of Bcl-2 expression and up-regulation of Bax. In another study, a peptide from amphibian skin, induced apoptosis in bladder cancer cells by decreasing the expression of Bcl-2 and increasing the Bax expression. In the present study, conjugate 7 peptide down-regulates the mRNA expression of Bcl-2 significantly in MCF-7 cells (FIG. 3). At 50 and 100 μM concentrations, Bcl-2 expression was decreased down to 0.7 and 0.6 folds of control cells, respectively. Bcl-2 protein expression exactly correlates with mRNA expression, as evidenced by immunocytochemistry images (FIG. 9). Bcl-2 protein is an example of oncogenes that prevents the cell death by maintaining the integrity of mitochondrial membrane and to prevent mitochondria to release its protein (like cytochrome c) into the cytoplasm. Like other anti-apoptotic proteins, Bcl-2 inhibits the functioning of pro-apoptotic factors (e.g. Bax and Bak) and prevents their oligomerization. Bcl-2 can regulate both intrinsic and extrinsic modes of apoptosis by inhibiting the apoptosome activation or by inhibiting the apoptosome-independent pathway.

Few studies are available showing the modulation of Bax protein expression after anticancer peptide treatment. A cationic peptide is reported to induce cell death in human osteosarcoma U2OS cells through the activation of Bax regulated mitochondrial membrane permeabilization. Another study reveals that Bax expression was decreased in human neurons after amyloid-β peptide treatment isolated from Alzheimer's patient. In this study, Bax expression following treatment with conjugate 7 demonstrated no significant change at all test doses (FIG. 4). Since we have observed insignificant change in Bax gene expression after conjugate 7 treatment, therefore, Bax/Bcl-2 ratio was calculated (Table 4). Nevertheless, fluorescence microscope images for Bax expression showed significant increase in Bax protein expression (FIG. 10). Immunofluorescence images for Bax protein indicated the increase at 25 and 50 μM dose after treatment of conjugate 7. However, at higher doses, expression of Bax protein became limited to few spots due to 48 hour treatment time. Thus it can be concluded that after conjugate 7 treatment at mRNA and protein levels, decrease in Bax gene expression might be overcome by more decrease in Bcl-2 gene expression resulting in the favorable conditions that induce apoptosis or it can be proposed that conjugate 7 regulates the Bax expression after transcription. Another proposed mechanism is the release of Bax protein from other protein complexes or cellular structures after conjugate 7 treatment. An increase in Bax protein expression plays its conventional role in inducing apoptosis.

TABLE 3

Ratio of Bax/Bcl-2 gene expression in MCF-7 cell line

| | Bax (Mean ± St. Dev) | Bcl-2 (Mean ± St. Dev) | Bax/Bcl-2 |
|---|---|---|---|
| Control | 1.00 ± 0.04 | 1.00 ± 0.11 | 0.99 |
| 25 μM | 0.88 ± 0.06 | 1.20 ± 0.08 | 0.73 |
| 50 μM | 0.75 ± 0.01 | 0.63 ± 0.11 | 1.20 |
| 100 μM | 0.74 ± .03 | 0.57 ± 0.17 | 1.30 |

Survivin is an inhibitor of apoptosis (IAP), It is reported that down regulation of survivin induce programmed cell death. In current study, conjugate 7 down regulated the survivin expression as compare to control cells. At 25 μM concentration, no change was observed (FIG. 5). However, at 50 and 100 μM doses, survivin expression decreased significantly down to 0.7 folds of control cells. Similarly, survivin protein expression also decreased showing a good correlation with mRNA levels. Micrographs for survivin showed the change in its arrangement with decrease in its expression after conjugate 7 treatment (FIG. 11). In control cells, survivin molecules were present in peripheral locations of the cell but after treatment these molecules became accumulated together due to shrinking of cells (also indicates apoptotic condition of the cells) and increase in intensity might be due to merging of several survivin-linked FITC molecules after rupturing of cells at these high concentrations. These results for survivin indicate that survivin expression down regulated MCF-7 cells and play its part in programmed cell death at transcriptional and translational levels. Survivin inhibits apoptosis at several levels including inhibition of caspase-8 mediated extrinsic pathway as well as by engaging the mitochondrial (intrinsic) pathway at the convergence point of both pathways which involves the activation of effecter caspases (caspase-3 and -7).

Caspases have an important role in apoptosis. Among various caspases, Caspase-3 is the most important among all caspases which are involved in apoptosis including DNA fragmentation. Previous studies indicated the effect of peptides on caspase-3 activation resulting in apoptotic cell death. In our study, peptide conjugate 7 caused the induction of apoptosis in MCF-7 cells through the up-regulation of caspase-3 gene expression upto 4 to 5 folds in comparison with untreated control cells in MCF-7 cells. (FIG. 6). Increase in caspase-3 expression was clearly observed by fluorescence micrographs for nuclear staining (DAPI) after action of conjugate 7. These images indicate with increasing dose, decrease in cell number, nuclear condensation and formation of apoptotic bodies (FIG. 7). As an important constituent of cytoskeleton and one of the substrate of caspase-3 activated enzymes, β-actin expression was also checked. Immunofluorescence images showed that in MCF-7, the cytoskeleton structure was intact and round in shape indicating active growth and proliferation (FIG. 8). Micrographs for β-actin protein clearly shows the deterioration of the cytoskeleton structure following conjugate 7 treatment and at higher doses undefined structures were seen along with decrease in the number of cells. This destruction of β-actin structure proved the process of apoptosis mediated through the activity of caspase-3 activation. This up-regulation of caspase-3, formation of apoptotic bodies and degradation of β-actin in cytoskeleton validate the TUNEL assay results and confirms the induction of apoptosis. Caspase-3 up-regulation by conjugate 7 was also validated by the immunostaining showing structural deterioration of β-actin protein and by condensation of nuclear material as indicated by DAPI staining, confirming the apoptosis induction as a type of cell death induced by conjugate 7. The new conjugate 7 developed from SEQ ID NO: 4 with breast cancer targeting peptide was found selective inhibitor for breast cancer cells and it was found to induce apoptosis in MCF-7 cells through the up-regulation of caspase-3 expression and due to the inhibition of anti-apoptotic gene expression.

EXPERIMENTAL SECTION

General Experimental Procedures.

All amino acids, coupling reagents, and resins were procured from Novabiochem, and Chem-impex. The $^1$H and $^{13}$C NMR spectra were recorded on Bruker NMR spectrometers, operating at 600 MHz and 125 MHz, respectively. HR-FABMS was recorded on JEOL JMS HX 110 mass spectrometers.

Mass Spectrometric Analysis of Peptides.

Matrix-assisted laser desorption/ionization (MALDI) was carried out on an Ultraflex III TOF/TOF (Bruker Daltonics, Bremen, Germany) mass spectrometer. All peptides that are soluble in 0.1% TFA/H$_2$O/ACN 40:60 were mixed with 0.5 μL of the matrix (HCCA) solution (saturated solution in 0.1% TFA/CH$_3$CN, 2:1) and deposited on a MALDI plate. Mass was recorded with the ion source 1 (IS1) set to 25.00 kV and ion source 2 (IS2) set to 21.50 kV and without delay extraction (DE). External calibration using peptide calibration standard (Bruker, Daltonics, Bremen, Germany), and all further data processing was carried out by using Flex analysis software and for data acquisition by Flex control.

ESI-QTOF-MS spectra were recorded on a Q-STAR XL mass spectrometer (Applied Biosystems). Each peptide dissolved in 0.1% TFA/H$_2$O/ACN 40:60 was infused directly into the mass spectrometer at a flow rate of 3 µL/min to acquire full scan and product ion mass spectra. The electrospray voltage at the spraying needle was optimized at 5500 V.

Peptide Synthesis.

The peptides 1-8 (FIG. 1) were synthesized by using Fmoc chemistry on Rink amide MBHA resin (Novabiochem, 0.51 mmol/g) and purification of peptides was achieved by using 0.1% TFA in H$_2$O/60% ACN on RP-HPLC (LC-900 Japan Analytical Instrument) at a flow rate of 4 mL/min.

Cell lines and Materials

NIH-3 T3 (ATCC® CRL-1658™), H460 (ATCC® HTB-177™) and the human breast cancer cell line MCF-7 was purchased from ATCC (ATCC® HTB-22™). MCF-7 cells are useful for in vitro breast cancer studies because these cells retain many ideal characteristics particular of differentiated mammary epithelium. RPMI-1640 medium, FBS, and anti-human-Bcl-2 primary antibody and anti-human-beta-actin primary antibody in mouse were purchased from Sigma-Aldrich (USA). The TRIzol reagent and Alexa Fluor® 488 goat anti-mouse secondary antibody were obtained from Invitrogen (USA). Anti-human-Bax primary antibody was procured from Santa Cruz Biotechnologies (USA). DAPI, TUNEL Assay kit, cDNA synthesis kit and SYBR green master mix, and rabbit monoclonal anti-survivin primary antibody were purchased from MP Biomedical (USA), Merck (USA), Fermentas (USA), and Abcam (USA) respectively.

[3-(4, 5-dimethylthiazol-2-yl)-2,5-diphenyl Tetrazolium bromide] MTT Assay

The cytotoxic as well as antiproliferative effect of peptides was determined using MTT [3-(4, 5-dimethylthiazol-2-yl)-2, 5-diphenyl tetrazolium bromide] colorimetric assay. MCF-7, NIH-3T3, HeLa and H460 cells were cultured and after confluency, cells were used to test the cytotoxicity by MTT assay. Briefly (3×10$^4$/mL) of MCF-7 and (2×10$^4$/mL) cells of NIH-3T3, HeLa and H460 were seeded in 96-wells plate and incubated at 37° C. in 5% CO$_2$ for 24 h. The MCF-7 cells were then treated with different doses of peptides and re-incubated in 5% CO$_2$ at 37° C. for 48 hours. The other cell lines were tested with different doses (1, 10 and 100 Untreated control cells were treated with complete medium while vehicle control cells with medium containing 0.5% DMSO. Doxirubicin, cyclohexamide, and cisplatin were used as standard drugs for MCF-7, HeLa, NIH-3T3 and H460, respectively. After 48 hours, media containing compounds were removed and 200 µl medium containing (0.5 mg/ml) MTT was added to each well and re-incubated for 4 h at 37° C. in 5% CO$_2$. After 4 hours, MTT containing media were removed and formazan crystals were solubilized in pure DMSO and absorbance was measured using photometer (Thermofisher, USA) at 550 nm wavelength. Experiment was performed three times and all doses were repeated in triplicate and the calculations were done using formula for percent inhibition.

$$\text{Percent Inhibition} = \frac{(\text{Absorbance of control cells} - \text{Absorbance of treated cells}) \times 100}{\text{Absorbance of control cells}}$$

The viability of DoHH2 cells was determined by Alamar blue assay. Briefly 200 µl of 1×10$^5$ cells/ml were incubated with different concentrations of compounds for 24 hours. A one-tenth volume of Alamar blue was then added and the incubation continued for 4 hrs. Absorbance was read in spectrophotometer at wavelengths of 570 nm and 600 nm.

DNA Fragmentation Assay

DNA fragmentation occurs in the last stages of apoptosis. To assess the nature of cell death by active peptides (peptide SHa 4 and conjugate 7), TUNEL assay was performed. For this assay, MCF-7 cells were cultured in 6-well plate at a density of 1×10$^6$ cells/ml/well and kept at 37° C. overnight in 5% humidified CO$_2$. Next day, seeded cells were treated with 0, 25, 50 and 100 µM concentrations of peptideSHa 4 and conjugate 7 for 48 hours. Then, cells fixation was done with 1% paraformaldehyde and kept in ice 60 minutes and then centrifuged for 5 minutes at 3000 RCF. Cell pellets were washed in PBS and 50 µL of staining solution [containing reaction buffer, terminal deoxynucleotidyl transferase (TdT) enzyme, and deoxyuridine triphosphate labeled with fluorescein (F-dUTP)] added to the pellet and placed 37° C. for 90 minutes. After incubation, cells were rinsed to remove the stain and PI/RNase solution was incubated with cells at 1 hour. Flow cytometric analysis was performed using FACS Calibur instrument. Initially, singlet cells were gated by excluding doublets. Main window was set as a dot plot having FL-2 filter (for PI) on X-axis and FL-1 filter (for FITC) on Y-axis. Total 95% cells were gated on FSC/SSC dot plot and 10000 cells were counted during each analysis.

RNA Isolation and Complementary DNA Synthesis

The MCF-7 cells were seeded (1×10$^6$ cells/well) in 6-well plate and kept in 5% CO$_2$ at 37° C. for overnight incubation. Next day, cells were treated with medium containing 0, 25, 50 and 100 µM dose of conjugate 7 for 24 hours. Total RNA was isolated using TRIzol reagent by following the manufacturer's instructions. The isolated RNA was quantified using NANOdrop® and 260/280 ratio was calculated for RNA purity. Agarose (1.2%) gel electrophoresis was run to determine the integrity of RNA isolated at 70 volts for 45 minutes. RNA samples (1000 ng) with good integrity were used to synthesize cDNA using RevertAid® first strand kit (ThermoScientific).

Gene Expression Analysis

Real time gene expression analysis before and after treatment with conjugate 7 was performed on Stratagene Mx3000p (Agilent technologies, USA) using Maxima SYBR green (Fermentas, USA). Table 5 shows the primer sequences used in this study. Anti-apoptotic genes included in this analysis were Bcl-2 and survivin, however, pro-apoptotic genes were Bax and caspase-3. For the normalization of data, GAPDH was used as a housekeeping gene. All the primers were designed to have the melting temperature between 55 to 60° C. Thermal-cycling conditions were set as 95° C. for 10 minutes (pre-denaturation, 1 cycle), 95° C. for 15 seconds, 60° C. for 30 seconds, and 72° C. for 30 seconds (40 cycles). Melting curve temperatures were 95° C., 60° C. and 95° C. for 14 seconds each. At the end of each extension cycle, SYBR green signals were detected and converted automatically into ct-values. Fold change was calculated manually by using ΔΔct method:

Fold change=$2^{-\Delta\Delta ct}$

Where ΔΔct=[ct of treated for gene of interest−ct of untreated for gene of interest]−[ct of treated for GAPDH−ct of untreated for GAPDH]

Immunocytochemistry

To confirm the gene expression analysis results, change in Bax, Bcl-2, survivin and beta-actin protein expression after conjugate 7 treatment was checked through immunocytochemistry using fluorescence microscope (Nikon-90i, Japan) coupled with NIS-Element Software (Nikon, Japan). Chambered slides were used to culture MCF-7 cells at a density of 4×104 cells/well. Next day, cells were incubated with 25, 50 and 100 µM doses for 48 hours. Control cells were incubated with medium only. Then, cells were washed with PBS twice and fixed with paraformaldehyde (1%) for 30 Minutes. Triton-X100 (0.5%) was used to increase the cellular membrane permeabilization for 5 minutes. Blocking was done for 10 minutes with ROTI® reagent(Carl Roth, Germany). Cells were incubated for 90 minutes with their respective primary monoclonal antibodies (1:200 dilutions). Subsequently, cells were incubated with secondary antibodies (1:200 dilution) having fluorophores attached (Alexa Fluor-488) for 45 minutes. A set of control and treated cells were also stained with DAPI instead of antibodies. Slides were washed twice with PBS and then mounted. Images were taken using green and blue channels under 20× lens (200× of original size).

Statistical Analysis.

The data were statistically analyzed using SPSS and Microsoft Excel. Mean and standard deviation were calculated as representatives of data. One-way ANOVA with Tukey's test was utilized to determine p-values for the significance of data.

TABLE 5

List of primers

| S. No | Primer | Left | Right |
|---|---|---|---|
| 1 | Bcl-2 | 5'-[SEQ ID NO. 77: gaggattgtggcccttattg]-3' | 5'-[SEQ ID NO. 78: acagttccacaaaggcatcc]-3' |
| 2 | CASPASE-3 | 5'-[SEQ ID NO. 79: atggaagcgaatcaatggac]-3' | 5'-[SEQ ID NO. 80: atcacgcatcaattccacaa]-3' |
| 3 | Bax | 5'-[SEQ ID NO. 81: agatcatgaagacaggggcc]-3' | 5'-[SEQ ID NO. 82: gcaatcatcctctgcagctc]-3' |
| 4 | Survivin | 5'-[SEQ ID NO. 83: cagagtccctggctcctctac]-3' | 5'-[SEQ ID NO. 84: ggctcactgggcctgtcta]-3' |
| 5 | GAPDH | 5'-[SEQ ID NO. 85: ccagaacatcatccctgcct]-3' | 5'-[SEQ ID NO. 86: cctgcttcaccaccttcttg]-3' |

---

What is claimed is:

1. A non-natural peptide of between 13 and 100 amino acids selected from the group of peptides consisting of:
   a non-natural peptide containing the sequence F-L-S-a-I-V-G-M-L-G-K-L-F (SEQ ID NO: 2) or a pharmaceutically acceptable salt thereof;
   a non-natural peptide F-L-S-G-I-V-a-M-L-G-K-L-F (SEQ ID NO: 3) or a pharmaceutically acceptable salt thereof;
   a non-natural peptide F-L-S-G-I-V-G-M-L-a-K-L-F (SEQ ID NO: 4) or a pharmaceutically acceptable salt thereof;
   a non-natural peptide F-L-S-a-I-V-a-M-L-G-K-L-F (SEQ ID NO: 5) or a pharmaceutically acceptable salt thereof;
   a non-natural peptide F-L-S-a-I-V-a-M-L-a-K-L-F (SEQ ID NO: 6) or a pharmaceutically acceptable salt thereof;
   a non-natural peptide conjugate (conjugate 7) consisting of SEQ ID NO: 4 conjugated through its Lys residue with a ligand having sequence of W-L-E-A-A-Y-Q-K-F-L (SEQ ID NO. 9), or a pharmaceutically acceptable salt thereof; and
   a non-natural peptide conjugate (conjugate 8) consisting of a dimeric form of SEQ ID NO: 4 conjugated at C-terminal through lysine with a ligand having sequence of W-L-E-A-A-Y-Q-K-F-L, (SEQ ID NO. 9) or a pharmaceutical salt thereof.

2. The non-natural peptide according to claim 1, wherein said pharmaceutically acceptable salt is a hydrochloric acid salt, hydrobromic acid salt, sulfuric acid salt, phosphoric acid salt, acetic acid salt, citric acid salt, maleic acid salt, malic acid salt, succinic acid salt, ascorbic acid salt, tartaric acid salt, sodium salt, potassium salt, calcium salt, magnesium salt or ammonium salt.

3. A method for treating cancer by administering a therapeutically effective dose of a non-natural peptide according to claim 1 to a subject in need of said treatment, wherein the cancer is selected from the group consisting of breast, cervical and lung cancer.

* * * * *